United States Patent [19]

Thomason et al.

[11] Patent Number: 5,175,255
[45] Date of Patent: Dec. 29, 1992

[54] METHODS FOR PURIFICATION OF PLATELET-DERIVED GROWTH FACTOR

[75] Inventors: Arlen R. Thomason, Thousand Oaks; Margery A. Nicolson, Pacific Palisades, both of Calif.

[73] Assignee: Amgen Inc., Thousand Oaks, Calif.

[21] Appl. No.: 25,344

[22] Filed: Mar. 23, 1987

[51] Int. Cl.$^5$ .......................... C07K 3/20; C07K 3/18
[52] U.S. Cl. ................................ 530/380; 530/399; 530/417; 530/427; 530/829; 530/350; 530/387.3; 530/412; 530/388.25; 424/85.8; 514/12; 514/8; 435/69.1
[58] Field of Search ............. 530/380, 399, 417, 417, 530/829, 412, 387, 350; 424/101, 85.8; 514/8, 12

[56] References Cited

U.S. PATENT DOCUMENTS 4,479,896 10/1984 Antoniades ..................... 530/427

FOREIGN PATENT DOCUMENTS 2173803A 10/1986 United Kingdom .

WO83/03678 10/1983 World Int. Prop. O. .

OTHER PUBLICATIONS

Lars et al., Chem. Abst., 109, 155(1988), entry No. 6724b.
Deuel et al, The Journal of Biological Chemistry, vol. 256, No. 17, 8896-8899(1981).

*Primary Examiner*—F. T. Moezie
*Attorney, Agent, or Firm*—Julia E. Abers; Steven M. Odre

[57] ABSTRACT

Monoclonal antibodies specific for epitopes found on the B chain of PDGF (including v-sis, c-sis and platelet-derived forms) may be bound to columns and used for purification of rPDGF B. A solution containing a polypeptide possessing at least part of the structural conformation of rPDGF B is passed over such a column and the rPDGF B is bound to the antibody. The rPDGF B may then be eluted from the column to yield rPDGF B of greater than 95% purity as determined by SDS-PAGE.

18 Claims, 14 Drawing Sheets

1   MetLeuLeuThrSerSerLeuHisHisProArgHisGlnMetSerProGlySerTrpLys   20

21  LysLeuIleIleLeuLeuSerCysValPheGlyGlyGlyGlyThrSerLeuGlnAsnLys   40

41  AsnProHisGlnProMetThrLeuThrTrpGlnGlyAspProIleProGluLeuTyr      60

61  LysMetLeuSerGlyHisSerIleArgSerPheAsnAspLeuGlnArgLeuLeuGlnGly   80

81  AspSerGlyLysGluAspGlyAlaGluLeuLeuAspLeuAsnMetThrArgSerHisSerGly  100

101 GlyGluLeuGluSerLeuLeuAlaArgGlyLysArgGlyLysSerLeuSerValAlaGlu   120

121 ProAlaMetIleAlaGluCysLysThrArgThrGluValPheGluIleSerArgArgLeu   140

FIG. 1

141 IleAspArgThrAsnAlaAsnPheLeuValTrpProProCysValGluValGlnArgCys 160
161 SerGlyCysCysAsnAsnArgAsnValGlnCysArgProThrGlnValGlnLeuArgPro 180
181 ValGlnValArgLysIleGluIleValArgLysLysProIlePheLysLysAlaThrVal 200
201 ThrLeuGluAspHisLeuAlaCysLysCysGluIleValAlaAlaAlaArgAlaValThr 220
221 ArgSerProGlyThrSerGlnGluGlnArgAlaLysThrThrGlnSerArgValThrIle 240
241 ArgThrValArgValArgArgProProLysGlyLysHisArgLysCysLysHisThrHis 260
261 AspLysThrAlaLeuLysGluThrLeuGlyAla

FIG. 1 CONT.'

```
  1  MetAsnArgCysTrpAlaLeuPheLeuSerLeuCysCysTyrLeuArgLeuValSerAla                      20
 21  GluGlyAspProIleProGluGluLeuTyrGluMetLeuSerAspHisSerIleArgSer                      40
 41  PheAspAspLeuGlnArgLeuLeuHisGlyAspProGlyGluGluAspGlyAlaGluLeu                      60
 61  AspLeuAsnMetThrArgSerHisSerGlyGlyGluLeuGluSerLeuAlaArgGlyArg                      80
 81  ArgSerLeuGlySerLeuThrIleAlaGluProAlaMetIleAlaGluCysLysThrArg                     100
101  ThrGluValPheGluIleSerArgArgLeuIleAspArgThrAsnAlaAsnPheLeuVal                     120
```

FIG. 2

```
121  TrpProProCysValGluValGlnArgCysSerGlyCysCysAsnAsnArgAsnValGln   140

141  CysArgProThrGlnValGlnLeuArgProValGlnValArgLysIleGluIleValArg   160

161  LysLysProIlePheLysLysAlaThrValThrLeuGluAspHisLeuAlaCysLysCys   180

181  GluThrValAlaAlaAlaArgProValThrArgSerProGlyGlySerGlnGluGlnArg   200

201  AlaLysThrProGlnThrArgValThrIleArgThrValArgValArgArgProProLys   220

221  GlyLysHisArgLysPheLysHisThrHisAspLysThrAlaLeuLysGluThrLeuGly   240

241  Ala
```

FIG. 2 CONT.

```
GGGGACCCCATTCCCGAGGAGCTTTATGAGATGCTGAGTGACCACTCGATCCGCTCCTTT
GlyAspProIleProGluGluLeuTyrGluMetLeuSerAspHisSerIleArgSerPhe

GATGATCTCCAACGCCTGCTGCACGGAGACCCCGGAGAGGAAGATGGGGCCGAGTTGGAC
AspAspLeuGlnArgLeuLeuHisGlyAspProGlyGluGluAspGlyAlaGluLeuAsp

CTGAACATGACCCGCTCCCACTCTGGAGGCGAGCTGGAGAGCTTGGCTCGTGGAAGAAGG
LeuAsnMetThrArgSerHisSerGlyGlyGluLeuGluSerLeuAlaArgGlyArgArg

AGCCTGGGTTCCCTGACCATTGCTGAGCCGGCCATGATCGCCGAGTGCAAGACGCGCACC
SerLeuGlySerLeuThrIleAlaGluProAlaMetIleAlaGluCysLysThrArgThr

GAGGTGTTCGAGATCTCCCGGCGCCTCATAGACCGCACCAACGCCAACTTCCTGGTGTGG
GluValPheGluIleSerArgArgLeuIleAspArgThrAsnAlaAsnPheLeuValTrp

CCGCCCTGTGTGGAGGTGCAGCGCTGCTCCGGCTGCTGCAACAACCGCAACGTGCAGTGC
ProProCysValGluValGlnArgCysSerGlyCysCysAsnAsnArgAsnValGlnCys

CGCCCCACCCAGGTGCAGCTGCGACCTGTCCAGGTGAGAAAGATCGAGATTGTGCGGAAG
ArgProThrGlnValGlnLeuArgProValGlnValArgLysIleGluIleValArgLys

AAGCCAATCTTTAAGAAGGCCACGGTGACGCTGGAAGACCACCTGGCATGCAAGTGTGAG
LysProIlePheLysLysAlaThrValThrLeuGluAspHisLeuAlaCysLysCysGlu

ACAGTGGCAGCTGCACGGCCTGTGACCCGAAGCCCGGGGGGTTCCCAGGAGCAGCGAGCC
ThrValAlaAlaAlaArgProValThrArgSerProGlyGlySerGlnGluGlnArgAla

AAAACGCCCCAAACTCGGGTGACCATTCGGACGGTGCGAGTCCGCCGGCCCCCCAAGGGC
LysThrProGlnThrArgValThrIleArgThrValArgValArgArgProProLysGly

AAGCACCGGAAATTCAAGCACACGCATGACAAGACGGCACTGAAGGAGACCCTTGGAGCC
LysHisArgLysPheLysHisThrHisAspLysThrAlaLeuLysGluThrLeuGlyAla

TAGGGGCATCGGCAGGAGAGTGTGTGGGCAG
End
```

FIG.4

```
             10                    30                       50
TCGACAGTCGGCATGAATCGCTGCTGGGCGCTCTTCCTGTCTCTCTGCTGCTACCTGCGT
     GTCAGCCGTACTTAGCGACGACCCGCGAGAAGGACAGAGAGACGACGATGGACGCA
             MetAsnArgCysTrpAlaLeuPheLeuSerLeuCysCysTyrLeuArg 70                 90
CTGGTCAGCGCCGAGGGGGACCCCATTCCCGAGGAGCT
GACCAGTCGCGGCTCCCCCTGGGGTAAGGGCTCC
LeuValSerAlaGluGlyAspProIleProGluLeu
```

FIG.8

MetAsnArgCysTrpAlaLeuPheLeuSer
LeuCysCysTyrLeuArgLeuValSerAlaGluGlyAspProIleProGluGluLeuTyr
LysMetLeuSerGlyHisSerIleArgSerPheAsnAspLeuGlnArgLeuLeuGlnGly
AspSerGlyLysGluAspGlyAlaGluLeuAspLeuAsnMetThrArgSerHisSerGly
GlyGluLeuGluSerLeuAlaArgGlyLysArgSerLeuGlySerLeuSerValAlaGlu
ProAlaMetIleAlaGluCysLysThrArgThrGluValPheGluIleSerArgArgLeu
IleAspArgThrAsnAlaAsnPheLeuValTrpProProCysValGluValGlnArgCys
SerGlyCysCysAsnAsnArgAsnValGlnCysArgProThrGlnValGlnLeuArgPro
ValGlnValArgLysIleGluIleValArgLysLysProIlePheLysLysAlaThrVal
ThrLeuGluAspHisLeuAlaCysLysCysGluIleValAlaAlaAlaArgAlaValThr
ArgSerProGlyThrSerGlnGluGlnArgAlaLysThrThrGlnSerArgValThrIle
ArgThrValArgValArgArgProProLysGlyLysHisArgLysCysLysHisThrHis
AspLysThrAlaLeuLysGluThrLeuGlyAla

FIG. 10

MetThrPheProAlaMetProLeuSerAsnLeuPheAlaAsnAlaValLeuArgAlaGln

HisLeuHisLeuLeuAlaAlaGluThrTyrLysGluPheGluArgThrTyrIleProGlu

AspGlnArgTyrThrAsnLysAsnSerGlnAlaAlaPheCysTyrCysGluThrIlePro

AlaProThrGlyLysAspAspAlaGlnGlnLysSerAspMetGluLeuLeuArgPheSer

LeuValLeuIleGlnSerTrpLeuThrProValGlnTyrLeuSerLysValPheThrAsn

AsnLeuValPheGlyThrSerAspArgValPheGluLysLeuLysAspLeuGluGluGly

IleSerArgArgLeuIleAspArgThrAsnAlaAsnPheLeuValTrpProProCysVal

GluValGlnArgCysSerGlyCysCysAsnAsnArgAsnValGlnCysArgProThrGln

ValGlnLeuArgProValGlnValArgLysIleGluIleValArgLysLysProIlePhe

LysLysAlaThrValThrLeuGluAspHisLeuAlaCysLysCysGluIleValAlaAla

AlaArgAlaValThrArgSerProGlyThrSerGlnGluGlnArgAlaLysThrThrGln

SerArgValThrIleArgThrValArgValArgArgProProLysGlyLysHisArgLys

CysLysHisThrHisAspLysThrAlaLeuLysGluThrLeuGlyAla

FIG.11

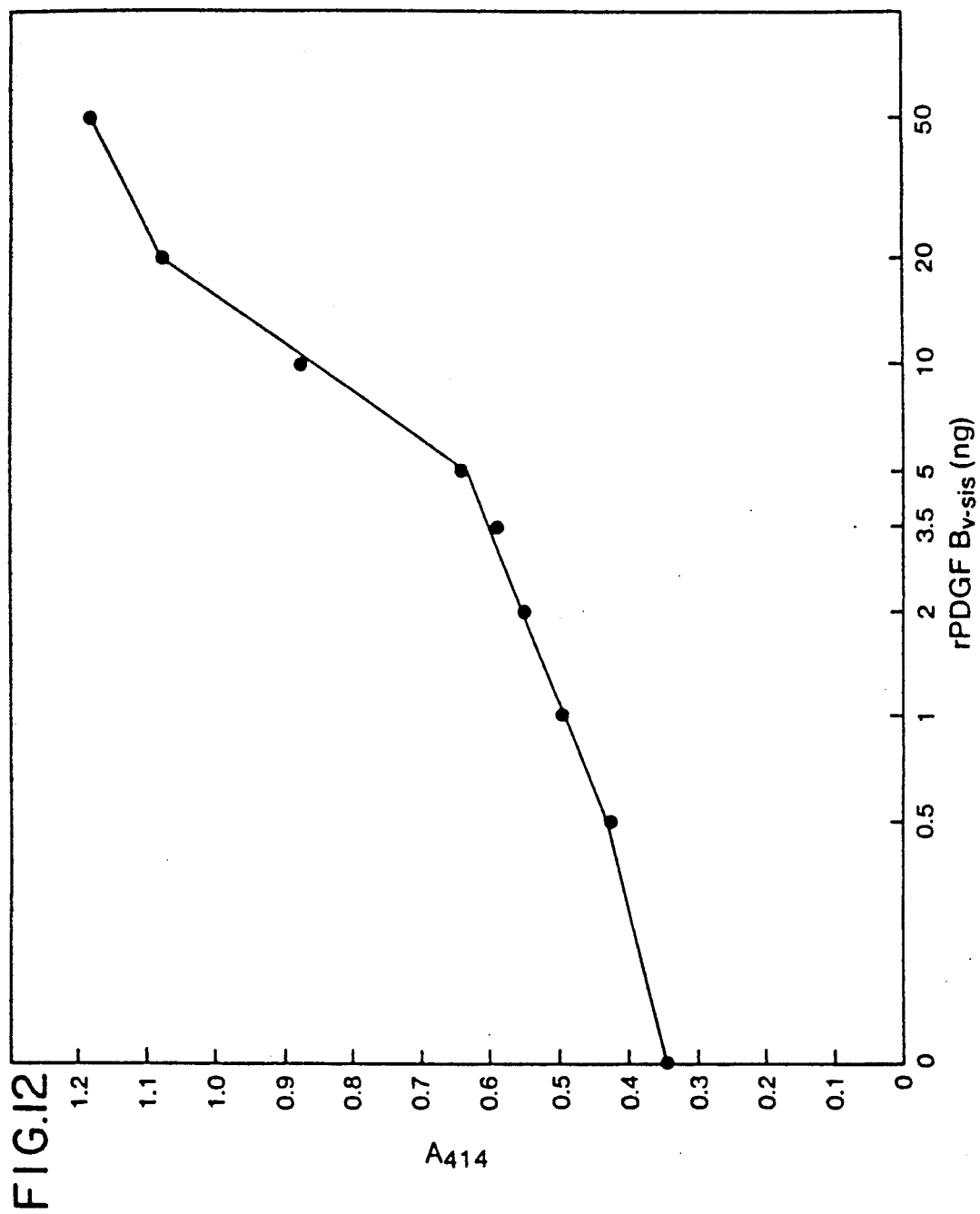

METHODS FOR PURIFICATION OF PLATELET-DERIVED GROWTH FACTOR

BACKGROUND

The present invention pertains in general to highly purified recombinant platelet-derived growth factor (rPDGF) and methods for obtaining such material. In particular, the present invention relates to affinity chromatographic purification of rPDGF employing monoclonal antibodies and to such monoclonal antibodies, as well as to a method of production of crude PDGF in quantities sufficient to be useful.

Ross et al., *Proc. Natl. Acad., Sci. U.S.A.* 71: 1207-1210 (1974) described platelet derived growth factor (PDGF) as a factor found in whole blood serum but not platelet-poor serum, which factor was able to support growth of fibroblasts in culture.

Unreduced PDGF is a 27-35 kd mw protein. The variation in the number of bands observed on some separating gels may be due to glycosylation differences, protease action during purification, or the presence of more than one molecular species. Reduction of PDGF yields 2 or more smaller bands on gels, in a molecular weight range of 10-18 kd. The model favored by most in the field is that the native 27-35 kd mw species consists of 2 smaller, dissimilar subunits of approximately 18 kd and 16 kd molecular weights, called respectively the "A" and "B" subunits (or alternatively PDGF A chain and PDGF B chain). Doolittle et al., *Science* 221: 275-76 (1983); and Waterfield et al., *Nature* 304: 2810-14 (1983) described the partial amino acid sequences of the two subunits of PDGF, indicating that the amino acid sequence of the PDGF B chain was more than 90% homologous with the predicted protein product of v-sis, the oncogene contained within the oncogenic simian sarcoma virus (SSV). The A chain was found to be approximately 60% homologous to the B chain.

Simian sarcoma virus was isolated from the fibrosarcoma of a woolly monkey. This virus causes oncogenic transformation of cells, and causes sarcomas in some animals. The complete SSV genome has been cloned and sequenced, and the oncogene region (v-sis) was identified and found to be potentially capable of coding for a fusion protein of 28-33 kd molecular weight. Antisera raised to peptides based on this sequence immunoprecipitated a protein of 28 kd from SSV-infected cells. This protein was called p28sis (Robbins et al., *Nature* 305:605-608 (1983)). Using v-sis as a probe, chromosomal clones corresponding to c-sis were isolated from a human liver library by Gallo et al. (*Nature* 292:31 (1981); and Josephs et al. *Science* 219:503-505 (1983)) and Aaronson et al. (*Cell* 37:123 (1983)). In addition, using v-sis as a probe, a number of human tumor cell lines were screened for expression of c-sis RNA by Gallo et al. (*Nature* 295:116-119 (1982)) and a high percentage of tumors of mesenchymal origin were found to contain a 4.2 kb c-sis RNA transcript.

Gallo et al. (*Science* 223:487-490 (1984)) disclosed the sequence of all six of the exons of the human liver c-sis chromosomal gene that are homologous to v-sis. This disclosed DNA sequence predicted a protein product almost identical to the published amino terminal sequence of the PDGF B chain. In addition, this DNA sequence predicted the remainder of the PDGF B chain amino acid sequence which had not been derived by protein sequencing.

Also, Josephs et al., *Science* 225: 636-639 (1984) disclosed a 2.7 kb cDNA clone from HUT102 tumor cells. While not a complete clone of the 4.2 kb RNA, it apparently contained all the sequence necessary for coding for an active PDGF B chain. When placed in a vector downstream from a SV40 early promoter, the vector was capable of transforming 3T3 cells.

PDGF and analogs thereof have been expressed in prokaryotic and eukaryotic cells transformed with vectors including exogenous genes. Murray et al., European Patent Application No. 177,957, Hannick et al., *Mol. Cell. Biol.*, 6: 1304-1314 (1986); Hannick et al., *Mol. Cell. Biol.*, 6: 1343-1348 (1986); King et al., *Proc. Int'l Acad. Sci. (U.S.A.)*, 82: 5295-5299 (1985); Kelly et al., *EMBO J.* 4: 3399-3405 (1985); Josephs et al., *Science*, 225: 636 (1984); Clarke et al., *Nature*, 308: 464 (1984); Gazit et al., *Cell* 39: 89-97 (1984); and Wang, *J. Biol. Chem.*, 259: 10645-10648 (1984). However none of these references disclose expression of more than 50 ng/ml of active PDGF in culture media. Procedures for purifying platelet PDGF include those described in Heldin et al., *Nature*, 319: 511 (1986); Antoniades, U.S. Pat. No. 4,479,896 and Raines et al., *Methods Enzymol.*, 109: 749 (1985); Deuel et al., (1981). J. Biol Chem. 256: 8896-99; Antoniades, (1981). Proc. Natl. Acad. Sci. U.S.A. 78: 7314-17, however these procedures did not provide for separation of mitogenically active PDGF A homodimers or PDGF B homodimers.

SUMMARY OF THE INVENTION

The present invention provides a purified and isolated polypeptide having a sufficient part of the structural conformation of rPDGF B, having an epitope for binding to a monoclonal antibody specific for an epitope of a B chain of PDGF, having one or more of the biological properties of naturally-occurring PDGF and being characterized by a purity of greater than 95% as determined by reducing SDS-PAGE As used herein, the term "rPDGF B" shall mean biologically active homodimers of recombinant PDGF B chain unless otherwise specified. Preferably the polypeptide of the present invention is the product of prokaryotic or eukaryotic expression of an exogenous DNA sequence carried on an autonomously replicating DNA plasmid or viral vector. In particular the polypeptide possesses the structural conformation of rPDGF $B_{v\text{-}sis}$ as set forth in FIG. 1 or any naturally occurring variant thereof or the polypeptide possesses the structural conformation of rPDGF $B_{c\text{-}sis}$ as set forth in FIG. 2 or any naturally occurring variant thereof.

The present invention further relates to a class of monoclonal antibodies having an affinity to specifically bind to an epitope found in the B chain of PDGF.

The present invention further provides for a method for purifying a polypeptide of the present invention comprising contacting a substrate-bound monoclonal antibody having an affinity to specifically bind to an epitope found in rPDGF B with a solution containing a polypeptide having at least one epitope found in rPDGF B and eluting the polypeptide from the substrate-bound monoclonal.

The present invention provides also a method for expression of rPDGF B in significant quantities which comprises introduction of a PDGF B gene in a suitable vector into Chinese hamster ovary (CHO) cells, followed by induction of gene amplification, to obtain quantities (>0.4 µg/10⁶ cells/24 h; concentration of >1 µg/ml in 5 day medium) of crude rPDGF B which can be subjected to the purification procedure described herein. The invention further relates to cell lines useful in such expression systems.

The present invention also provides a method for promoting wound healing comprising the step of administrating an effective amount of a polypeptide according to the present invention.

BRIEF DESCRIPTION OF DRAWINGS

FIG. 1 is the primary amino acid sequence of rPDGF $B_{v\text{-}sis}$;

FIG. 2 is the primary amino acid sequence of rPDGF $B_{c\text{-}sis}$;

FIG. 4 is the complete sequence of exons 2 through 6 from the clone of FIG. 3 which encode rPDGF B;

FIG. 8 is a DNA sequence coding for a putative, rPDGF $B_{c\text{-}sis}$ precursor amino terminal region;

FIG. 10 is the amino acid sequence of the predicted initial translation product of the cv-sis gene.

FIG. 11 is an amino acid sequence for the CGH/PDGF fusion protein CGPl; and

FIG. 12 is a graphic depiction of ELISA assay results employing monoclonal antibodies according to the present invention.

DETAILED DESCRIPTION

Figure 3:
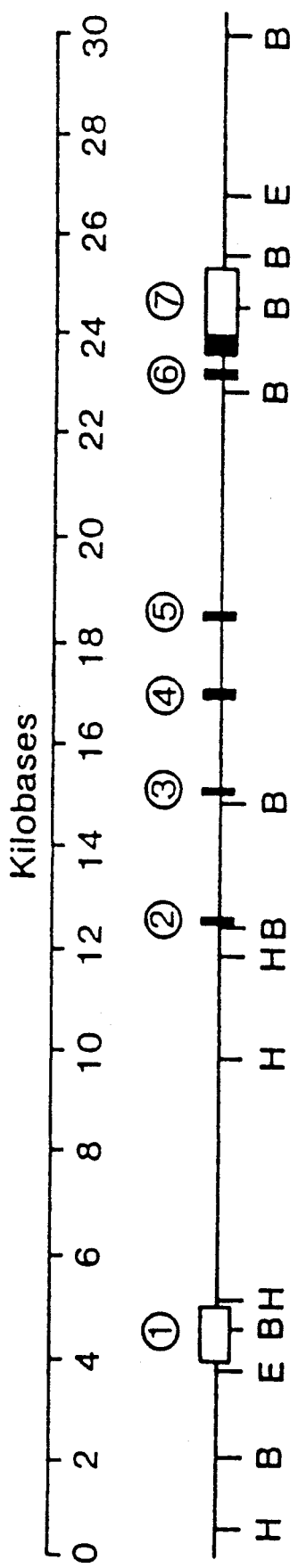
FIG. 3 is a schematic depiction of rPDGF $B_{c\text{-}sis}$ clone U2-OS56.1.

In accordance with the methods of the present invention, an isolated and purified polypeptide having at least part of the structural conformation of active rPDGF B was obtained. The polypeptides of the present invention comprise only part or all of rPDGF B and are essentially free of other PDGF related molecules, i.e., PDGF A chain, PDGF A homodimer and PDGF A,B heterodimers. The purified polypeptides of the present invention are characterized as having an epitope for binding to a monoclonal antibody specific for an epitope found in rPDGF B and have a purity of greater than 95% as determined by SDS-PAGE.

The method for purifying the polypeptides of the present invention comprises passing a solution containing the crude polypeptide over a chormatographic column to which is bound a monoclonal antibody specific for an epitope found in rPDGF B and then eluting the bound rPDGF B from the column.

As used herein, the terms "biologically active rPDGF B" or "active rPDGF B" refer to rPDGF B active in an in vitro mitogenic assay.

Representative of the monoclonal antibodies useful in methods of the present invention include a monoclonal antibody [30] expressed by a hybridoma deposited as ATCC No. HB 9366 with the American Type Culture Collection, 12301 Parklawn Drive, Rockville, Md. 20852 on Mar. 18, 1987; a monoclonal antibody [133] expressed by a hybridoma deposited as ATCC No. HB 9357 with the American Type Culture Collection, 12301 Parklawn Drive, Rockville, Md. 20852 on Mar. 12, 1987; a monoclonal antibody [155] expressed by a hybridoma deposited as ATCC No. HB 9354 with the American Type Culture Collection, 12301 Parklawn Drive, Rockville, Md. 20852 on Mar. 12, 1987; a monoclonal antibody [232] expressed by a hybridoma deposited as ATCC No. HB 9372 with the American Type Culture Collection, 12301 Parklawn Drive, Rockville, Md. 20852 on Mar. 18, 1987; a monoclonal antibody [52] expressed by a hybridoma deposited as ATCC No. HB 9361 with the American Type Culture Collection, 12301 Parklawn Drive, Rockville, Md. 20852 on Mar. 12, 1987; a monoclonal antibody [191] expressed by a hybridoma deposited as ATCC No. HB 9368 with the American Type Culture Collection, 12301 Parklawn Drive, Rockville, Md. 20852 on Mar. 18, 1987; a monoclonal antibody [20] expressed by a hybridoma deposited as ATCC No. HB 9355 with the American Type Culture Collection, 12301 Parklawn Drive, Rockville, Md. 20852 on Mar. 12, 1987; a monoclonal antibody [116] expressed by a hybridoma deposited as ATCC No. HB 9367 with the American Type Culture Collection, 12301 Parklawn Drive, Rockville, Md. 20852 on Mar. 18, 1987; a monoclonal antibody [198] expressed by a hybridoma deposited as ATCC No. HB 9369 with the American Type Culture Collection, 12301 Parklawn Drive, Rockville, Md. 20852 on Mar. 18, 1987; a monoclonal antibody [162] expressed by a hybridoma deposited as ATCC No. HB 9356 with the American Type Culture Collection, 12301 Parklawn Drive, Rockville, Md. 20852 on Mar. 12, 1987; a monoclonal antibody [296] expressed by a hybridoma deposited as ATCC No. HB 9370 with the American Type Culture Collection, 12301 Parklawn Drive, Rockville, Md. 20852 on Mar. 18, 1987; and a monoclonal antibody [219] expressed by a hybridoma deposited as ATCC No. HB 9371 with the American Type Culture Collection, 12301 Parklawn Drive, Rockville, Md. 20852 on Mar. 18, 1987.

The specific column and conditions for the chromatographic system employed are readily ascertained by one of ordinary skill in the art. Preferably an antibody affinity column is employed. Solvents useful in eluting the polypeptides of the present invention are readily ascertained by one of ordinary skill in the art and preferably include weak acids, i.e., acetic acid. A preferred method includes conducting the purification at a temperature of about 4° C.

As used herein the term "structural conformation" refers to the structure of a mitogenically active polypeptide having all or part of the amino acid sequence of rPDGF B.

The expression systems useful for the production of the polypeptides of the present invention comprise cell culture systems, preferably CHO cells. In addition to the expression systems herein described, other systems are contemplated by the present invention and include for example one or more of the following: modification of the sites for protease cleavage, use of an alternate leader sequence to increase level of secretion from host cells of the polypeptides of the present invention.

The present invention also provides cell lines producing rPDGF B including a CHO cell line producing a rPDGF $B_{v\text{-}sis}$ deposited as ATCC No. CRL 9359 with the American Type Culture Collection, 12301 Parklawn Drive, Rockville, Md. 20852 on Mar. 13, 1987 and a CHO cell line producing a rPDGF $B_{c\text{-}sis}$ deposited as ATCC No. CRL 9358 with the American Type Culture Collection, 12301 Parklawn Drive, Rockville, Md. 20852 on Mar. 13, 1987.

The present invention also provides rPDGF B$_{c\text{-}sis/v\text{-}sis}$ and rPDGF B$_{v\text{-}sis}$/chicken growth hormone (CGH) fusion polypeptides, DNA segments encoding them and transformation vectors containing such DNA segments. In particular, the present invention provides a cv-sis cell line deposited as ATCC Nos. CRL 9360 and a CGH vector deposited in *E. coli* AM7 as ATCC No. 67352 with the American Type Culture Collection, 12301 Parklawn Drive, Rockville, Md. 20852 on Mar. 13, 1987.

The biologically active rPDGF B produced by the prokaryotic or eukaryotic expression of the cloned rPDGF B genes of the present invention can be used for the in vivo treatment of mammalian species by physicians and/or veterinarians. The amount of active ingredient will, of course, depend upon the severity of the condition being treated, the route of administration chosen, and the specific activity of the rPDGF B, and will be determined by the attending physician or veterinarian. The amount of rPDGF B determined to produce a therapeutic response in a mammal is referred to as "PDGF B therapeutically effective" amount. Such therapeutically effective amounts are readily ascertained by one of ordinary skill in the art.

The rPDGF B may be administered by any route appropriate to the condition being treated. Preferably, the rPDGF B is applied topically to a wound. Compositions for topical application of the rPDGF B of the present are readily ascertained by one of ordinary skill in the art. It will be readily appreciated by those skilled in the art that the preferred route will vary with the condition being treated.

While it is possible for the rPDGF B to be administered as the pure or substantially pure compound, it is preferable to present it as a pharmaceutical formulation or preparation.

The formulations of the present invention, both for veterinary and for human use, comprise a therapeutically effective amount of rPDGF B as above described, together with one or more pharmaceutically acceptable carriers therefor and optionally other therapeutic ingredients. The carrier(s) must be "acceptable" in the sense of being compatible with the other ingredients of the formulation and not deleterious to the recipient thereof. Desirably the formulation should not include oxidizing or reducing agents and other substances with which peptides are known to be incompatible. The formulations may conveniently be presented in unit dosage form and may be prepared by any of the methods well known in the art. All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for parenteral administration conveniently comprise sterile aqueous solutions of the active ingredient with solutions which are preferably isotonic with the blood of the recipient. Such formulations may be conveniently prepared by dissolving solid active ingredient in water to produce an aqueous solution, and rendering said solution sterile may be presented in unit or multi-dose containers, for example sealed ampoules or vials. Formulations suitable for topical applications comprise a therapeutically effective amount of rPDGF with pharmaceutically acceptable topical adjuvants.

The following examples are provided to aid in the understanding of the present invention, the true scope of which is set forth in the appended claims. It is understood that modifications can be made in the procedures set forth, without departing from the spirit of the the invention. All temperatures are expressed in degrees Celsius and are uncorrected. The symbol for micron or micro, e.g., micro-liter, micromols, etc., is "u", e.g., ul, um, etc.

EXAMPLE 1

Subcloning and Sequence Analysis of c-sis and v-sis Genes

1(a) v-sis: The v-sis gene utilized in the present invention was derived from the plasmid pC60, a clone of the simian sarcoma virus retroviral genome (Wong-Staal et al., *Science* 213: 226-8 (1981)); obtained from R. Gallo (National Institutes of Health, Bethesda, Md.). A restriction fragment from pC60, spanning the region between the KpnI site at nucleotide 3505 (employing the numbering system of Devare et al., *Proc. Natl. Acad. Sci. U.S.A.* 80: 731-5 (1983)); and the XbaI site at nucleotide 4817, was subcloned into bacteriophage M13mp18. Five micrograms of pC60 DNA was digested with KpnI and XbaI, and the 1312 base pair fragment was purified by electrophoretic separation in and extraction from a low-melting temperature agarose gel, in accordance with the procedures described by Maniatis et al., Molecular Cloning: A Laboratory Manual. Cold Spring Harbor Laboratory, 1982. One microgram of M13mp18 DNA was also digested with KpnI and XbaI, followed by extraction with phenol/chloroform and ethanol precipitation. Thirty nanograms of the v-sis KpnI to XbaI fragment plus 50 ng of the KpnI and XbaI-cut M13mp18 DNA were ligated with T4 DNA ligase in 20 µl for 16 hours at 14° C. The ligated DNA was used to transform *E. coli* K12 strain JM103 (Messing et al., *Nucl. Acids Res.* 9: 309 (1981)) in the presence of 5-bromo, 4-chloro, 3-indole- β-D-galactoside (x-gal) and isopropyl β-D-thiogalactoside (IPTG). Clear plaques were selected and grown in liquid culture. DNA isolated from several of these phage was sequenced by the dideoxy chain termination method to confirm the identity of the cloned fragment. One of these phage clones, designated M13mp18/v-sis(Kpn-Xba).

1(b) c-sis: The c-sis gene which codes for the B chain of human PDGF, designated U2-OS56.1, contains 30.4 kb of human DNA and was isolated from a library constructed with DNA from the human osteosarcoma cell line U2-OS (ATCC No. HTB 96). The library was generated using the cosmid vector pTL5 (Lund et al., *Proc. Natl. Acad. Sci. (U.S.A.)*, 29: 520-524 (1982)) and the procedures described by Steinmetz et al., *Cell* 28: 489-498 (1982). The library was screened with a v-sis probe which had been subcloned from a clone of simian sarcoma virus obtained from Devare et al., *J. Virol.* 42: 1108 (1982) according to the procedure set forth in 1(a).

A map of clone U2-OS56.1 is shown in FIG. 3. The boxed areas in FIG. 3 represent exon sequences (Josephs et al., *Science* 223: 487 (1984) and Gazit et al., *Cell* 39: 89 (1984). Exons 2 through 7 are homologous to v-sis, and the junctions with nonhomologous regions represent the borders of the exons. Exon 1, while apparently necessary for initiation of translation of the RNA transcribed from this gene (Gazit et al., *Cell* 39: 89

(1984)), does not code for peptide sequences which appear in the final processed protein (Johnsson et al., Embo J. 3: 921 (1984)).

Restriction fragments containing exons 2-6 were subcloned into bacteriophage M13mp19 and sequenced by the dideoxy chain termination method according to the procedure of Sanger et al., *Proc. Natl. Acad. Sci. U.S.A.* 74: 5463 (1977). These exon sequences, which contain the entire region coding for the mature rPDGF B protein (Johnsson et al., *Embo J.* 3: 921 (1984)), were exactly the same as those previously published for a c-sis gene isolated from a human fetal liver chormosomal library (Josephs et al., *Science* 223: 487 (1984)). The complete sequence of exons 2 through 6 is shown in FIG. 4.

EXAMPLE 2

Construction of Mammalian Expression Vectors Containing rPDGF B Sequences

2(a) Construction of pDSVE: The vector chosen for expression of rPDGF B genes in Chinese hamster ovary DHFR$^-$ cells was called pDSVE. This vector was constructed using four basic DNA sequence elements. One of these elements provided DNA sequences necessary for selection and autonomous replication in bacterial cells. These characteristics are provided by the origin of replication and ampicillin-resistance gene DNA sequences in the region spanning nucleotides 2448 through 4362 (standard numbering system) of the plasmid pBR322. This 1918 base pair DNA fragment, derived from the pBR322 derivative pSV08 (obtained from Dr. R. Tjian, University of California, Berkeley), was structurally modified by the addition of the following HindIII linker immediately adjacent to nucleotide 2448:

5'-AAGCTTG-3'.

A second element provided DNA sequences constituting a viral promoter that is functional in mammalian and other vertebrate cells. A DNA fragment containing a simian virus 40 (SV40) early promoter was generated by first digesting SV40 DNA with restriction endonuclease enzyme PvuII, producing three PvuII/PvuII fragments of differing sizes. One of these fragments contained the sequence (HindIII at position number 5171 to PvuII at position number 270) which codes for the counterclockwise "early gene" promoter and origin of replication of the SV40 virus. An EcoRI linker was added to the 5' and 3' termini of each of the three fragments, thereby forming three EcoRI/EcoRI fragments of differing sizes. These fragments were digested with HindIII and a resulting 340 bp HindIII/EcoRI fragment was isolated by polyacrylamide gel electrophoresis.

A third element provided a signal for terminating transcription of genes inserted into the vector. A DNA fragment containing the terminator sequence of the early SV40 genes was obtained by first digesting the complete SV40 genome with restriction endonuclease HpaI, and then converting a blunt end into a SalI recognition site by the attachment of a SalI linker. This unligated HpaI/SalI SV40 sequence was thereafter digested with EcoRI, and the 2030 bp SalI/EcoRI fragment was isolated by agarose gel electrophoresis.

The fourth element contained in pDSVE provided a means for selecting mammalian cells containing the vector. The dihydrofolate reductase (DHFR) gene codes for an enzyme which allows cells to grow in media lacking thymidine and hypoxanthine, as well as allowing the cells to grow in media containing certain levels of the drug methotrexate. This gene comprised an approximately 2,500 bp mouse DHFR minigene, with EcoRI and HindIII restriction endonuclease sticky ends, isolated from plasmid pMG-1 as in Gasser et al., *Proc. Natl. Acad. Sci. (U.S.A.)* 79: 6522–6526 (1982).

Figure 5:
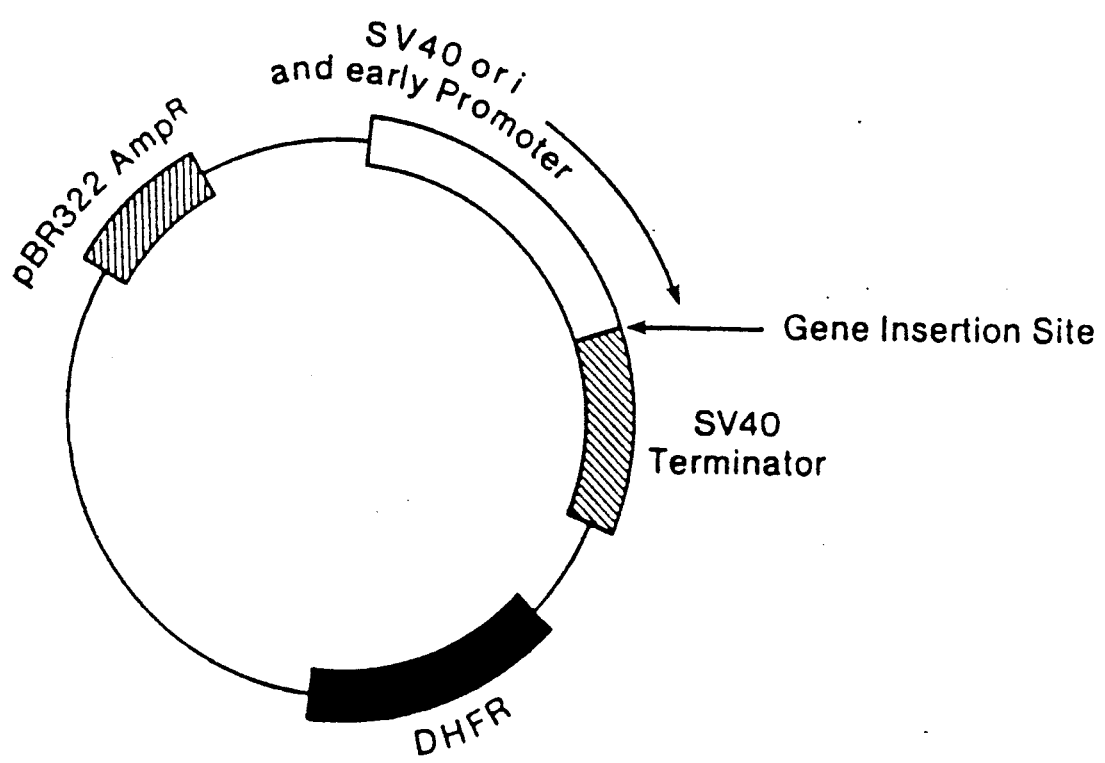
FIG. 5 is a schematic depiction of plasmid PDSVE.

The four DNA fragments containing these elements were ligated together with T4 DNA ligase, to produce the vector pDSVE. A diagram of this vector is shown in FIG. 5.

2(b) Construction of pDSVE/c-sis: A region of the c-sis cosmid clone U2-OS56.1 containing all of the sequences necessary for transformation of NIH-3T3 cells was subcloned into the SalI site of the plasmid pDSVLd (Lin et al., *Proc. Natl. Acad. Sci. U.S.A.* 82: 7580 (1985)). This region is spanned by the EcoRI sites at 3.9 kb and 26.85 kb on the U2-OS56.1 map in FIG. 3. The EcoRI ends of the c-sis fragment were converted to SalI ends prior to cloning of the c-sis fragment into pDSVLd. Three micrograms of cosmid U2-OS56.1 DNA was restricted with EcoRI, followed by phenol/chlorfrom extraction and ethanol precipitation. Flush ends on the double-stranded DNA were generated by filling in the single stranded regions in a 15 μl reaction containing the Klenow fragment of *E. coli* DNA polymerase I and all four deoxynucleoside triphosphates, in accordance with the procedures described by Maniatis, ibid. The reaction was terminated by heating the reaction mixture to 70° C. for 5 min. Synthetic DNA linkers containing the recognition site for the restriction endonuclease SalI were added to the blunt-ended c-sis fragment in a 21 μl reaction containing 1 μg of kinased linkers and T4 DNA ligase. After incubation overnight at 14° C., phenol/chloroform extraction and ethanol precipitation, the linkered DNA was restricted in a 100 μl reaction with 26 units of SalI for 3 hours. The restricted DNA was ethanol precipitated, dissolved in a small volume of buffer and electrophoresed in a 1% low-melting temperature agarose gel. The 23 kb band was cut out of the gel and purified in accordance with the procedures described by Maniatis, ibid. The 23 kb band was ligated to pDSVLd DNA which had been linearized with SalI, in a 20 μl reaction containing T4 DNA ligase. The ligated DNA was transformed into *E. coli* K12 strain DH1 (ATCC #33849). Ampicillin-resistant colonies were screened by hybridization with a $^{32}$P-labelled v-sis probe, according to procedures described by Maniatis ibid. A hybridizing clone was selected and plasmid DNA was prepared the clone. An insert from this clone, pDSVLd/c-sis, was excisable by restriction with SalI. Restriction mapping confirmed that this clone contained the expected 23 kb c-sis DNA fragment.

Surprisingly, pDSVLd/c-sis did not readily transform NIH-3T3 cells, and after introduction into COS-1 cells, or Chinese hamster ovary (CHO) cells pDSVLd/c-sis did not lead to production of a product having detectable levels of PDGF activity. A related plasmid constructed by Gazit et al. (ibid.) had been shown to be capable of transforming NIH-3T3 cells. Since pDSVLd/c-sis contained a 6.7 kb region of DNA between the putative exon 1 region and exon 2 region which was not present in the Gazit et al. construction, the possibility existed that this region contained sequences which inhibit expression of the c-sis gene in some mammalian cell types. A new mammalian c-sis expression vector was therefore constructed, in which the 6.7 kb DNA fragment between the HindIII sites at 5.2 kb and 11.9 kb on the c-sis map was deleted. This new vector was constructed using the mammalian expression vector pDSVE described in section 2(a) above. It was found that pDSVE usually yields higher expression levels of the inserted gene in CHO cells than did pDSVLd. One microgram of pDSVE was restricted with SalI, phenol/chloroform extracted amd ethanol precipitated, and used in the ligation described below.

For preparation of a fragment containing the putative exon 1 region of c-sis, 3 µg of pDSVLd/c-sis was restricted with BamHI and KpnI. The DNA fragments were separated by electrophoresis through a 0.7% low-melting temperature agarose gel. A 1.25 kb fragment representing the region between the BamHI site at 4.6 kb and the KpnI site at 5.85 on the c-sis map of FIG. 3 was excised from the gel and extracted as described by Maniatis, ibid. Seventy-five nanograms of this fragment was ligated with T4 DNA ligase in a 20 µl reaction to 75 ng of M13mp18 DNA which had been previously restricted with KpnI and BamHI. The ligated DNA was transformed into E. coli K12 strain JM103 as described above; several clear plaques were selected and grown in liquid culture. Replicative form (RF) double-stranded DNA was isolated from the infected cells and examined by restriction mapping with BamHI, KpnI, and HindIII. One clone exhibiting the correct pattern was selected for use in isolating a c-sis restriction fragment.

Four micrograms of M13mp18/c-sis(Bam-Kpn) RF DNA was restricted with SalI and HindIII. Restriction with SalI results in cutting at a site in the polylinker region of M13mp18 which is 13 base pairs away from the BamHI site at which the c-sis(Bam-Kpn) fragment was inserted. Restriction with HindIII results in cutting at the HindIII site of M13mp18. Importantly, restriction with HindIII results in cutting at the HindIII site within the c-sis(Bam-Kpn) fragment, at a position corresponding to 5.2 kb on the U2-OS56.1 map provided in FIG. 3. Thus, the effect of this procedure is to add a SalI site near the BamHI site at 3.9 kb on the map of U2-OS56.1 in FIG. 3. The 0.6 kb SalI to HindIII fragment was isolated from the reaction mixture by electrophoresis through a 1.0% low-melting temperature agarose gel and extraction. This fragment is referred to below as the Exon 1 fragment.

To obtain a DNA fragment containing c-sis exons 2-7 with the appropriate restriction site sticky ends, 4 µg of pDSVLd/c-sis was restricted with HindIII and SalI. The restricted DNA was electrophoresed through a 0.7% low-melting temperature gel and a 14.75 kb fragment representing the region between 11.9 kb and 26.85 kb on the U2-OS56.1 map of FIG. 3 was isolated. This fragment is referred to below as the Exon 2-7 fragment.

Figure 6:
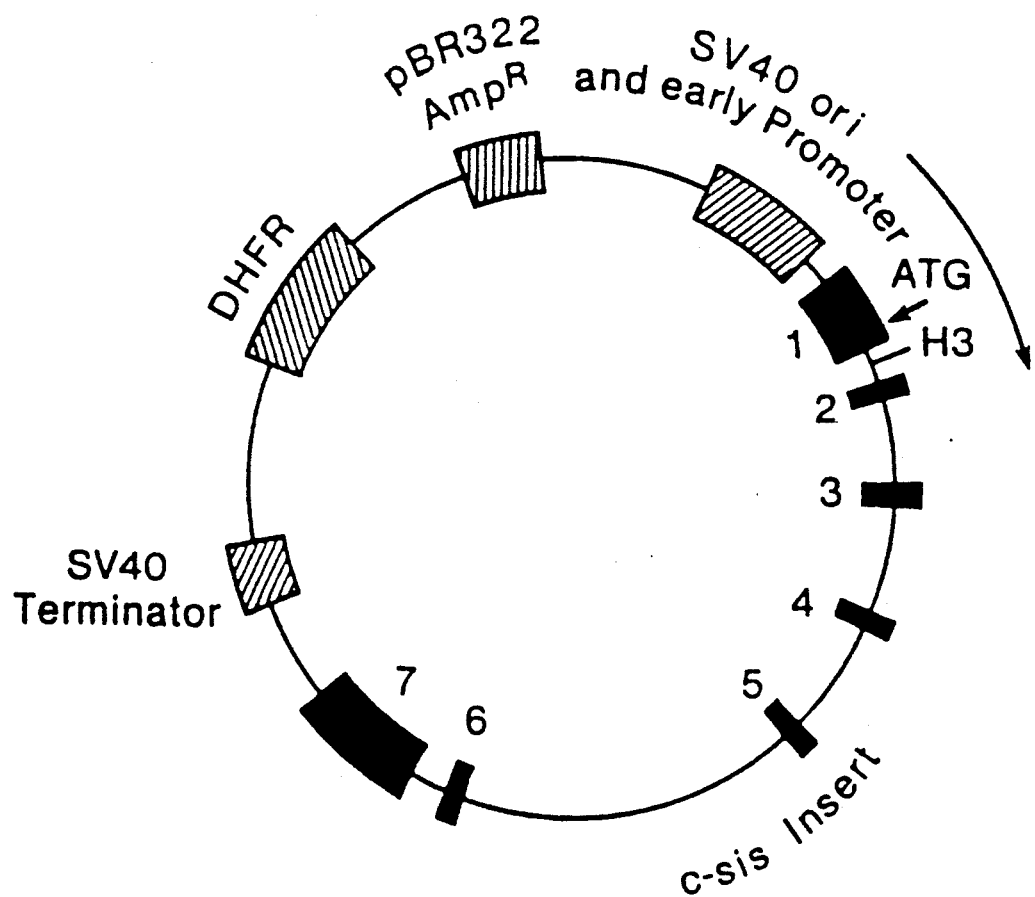
FIG. 6 is a schematic depiction of the plasmid pDSVE/c-sis.

In a final 20 µl ligation, 50 ng of SalI restricted pDSVE was mixed with 5 ng of the Exon 1 fragment and 80 ng of the Exon 2-7 fragment. After overnight reaction at 14° C. in the presence of T4 DNA ligase, the reaction mixture was transformed into E. coli K12 strain DH1. Two replica filters were made of ampicillin-resistant colonies. One filter was hybridized to a v-sis probe to detect the presence of the Exon 2-7 fragment, and the other was hybridized to a synthetic oligonucleotide complementary to a sequence contained in an upstream region of a c-sis cDNA clone (Josephs et al., *Science* 225: 636 (1984)). This oligonucleotide previously had been shown to hybridize to the Exon 1 fragment described above. A clone which hybridized to both probes was selected and grown up for plasmid isolation. Restriction analysis confirmed that this plasmid, called pDSVE/c-sis, contained elements arranged as depicted in FIG. 6.

Figure 7:
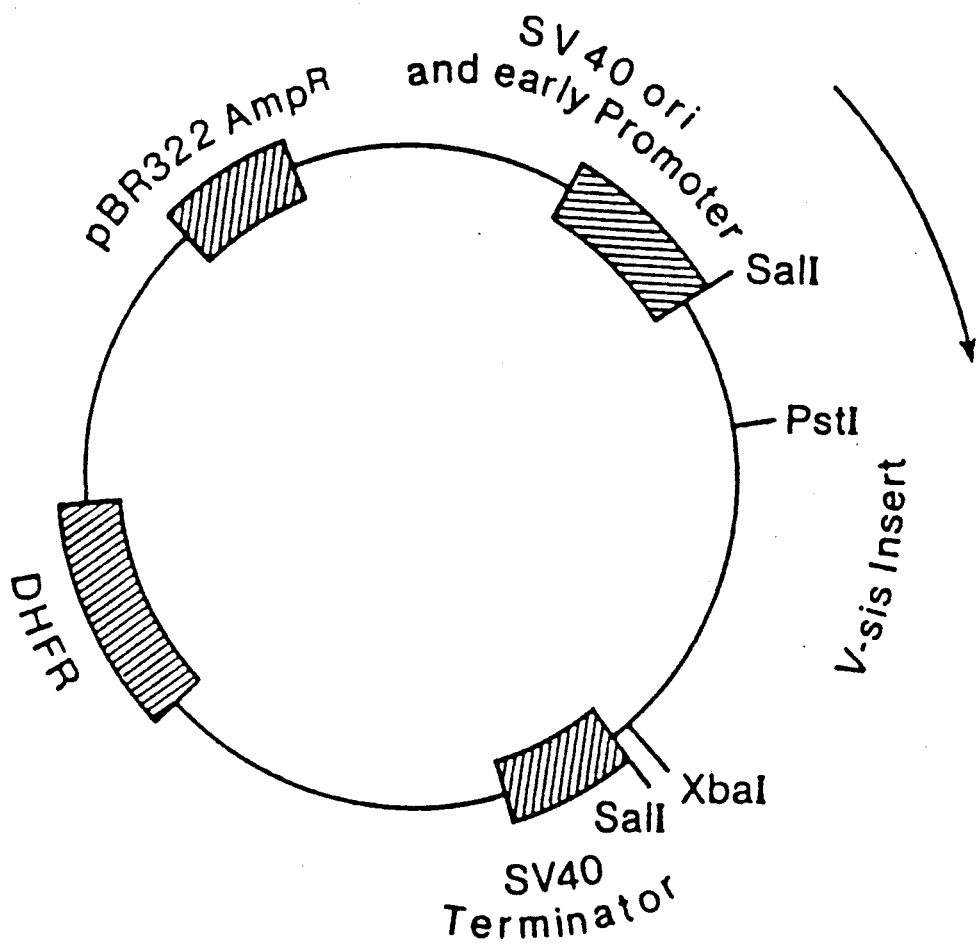
FIG. 7 is a schematic depiction of the plasmid pDSVE/v-sis.

2(c) Construction of pDSVE/v-sis: To construct a mammalian expression vector containing the v-sis gene that would use the translation initiation signal utilized by simian sarcoma virus, a DNA fragment containing the v-sis gene and 178 bp of SSV DNA upstream of it was inserted into pDSVE. The initial translation product resulting from transcription of this vector is a fusion of the SSV envelope glycoprotein and rPDGF B$_{v\text{-}sis}$ (Robbins et al., *Nature* 305: 605 (1983)). Processing of the amino terminal portion of the fusion product may then result in production of a mature rPDGF B protein lacking SSV envelope protein sequences. Two micrograms of the RF form of the M13mp18/v-sis(Kpn-Xba) subclone described in Example 1 was restricted with SalI. This results in release of a 1191 base pair fragment spanning the region between the SalI site at position 3633 of SSV (numbering system of Devare et al., ibid.), and the SalI site in the polylinker region of M13mp18; the latter site is 7 base pairs away from the XbaI site at which the v-sis gene was inserted. This fragment was purified by electrophoresis through a 0.7% low-melting temperature agarose gel, followed by excision of the band and extraction. Thirty-five nanograms of the fragment was ligated with T4 DNA ligase to 50 ng of SalI-cut pDSVE DNA in a 20 µl reaction at 14° C. for 16 h. The reaction product was transformed into E. coli K12 strain DH1; ampicillin-resistant colonies were screened by hybridization to a $^{32}$P-labelled v-sis probe, according to procedures described by Maniatis ibid. Several hybridizing clones were selected, grown in liquid culture, and subjected to plasmid isolation using standard procedures. The plasmids were mapped with the restriction enzymes HindIII, XbaI and PstI to identify clones containing inserts in the correct orientation for transcription by the SV40 early promoter in pDSVE. One such clone was named pDSVE/v-sis and was used in the examples described below. Its structure is diagrammed in FIG. 7.

2(d) Construction of pDSVE/cv-sis: To construct a mammalian expression vector in which the mature rPDGF B protein region is encoded by the v-sis gene, but the translation initiation signal and amino terminal region of the rPDGF B pre-protein is encoded by the c-sis gene, the following procedure may be used. One microgram of pDSVE was linearized with SalI, followed by phenol/chloroform extraction and ethanol precipitation. Three micrograms of the RF form of the M13mp18/v-sis(Kpn-Xba) subclone described in Example 1 was restricted with SstI and SalI. This results in the release of a 991 bp fragment spanning the region between the SstI site at position 3833 of SSV (Devare et al., ibid., numbering system) and the SalI site in the polylinker region of M13mp18. The latter site is 7 bp away from the XbaI site at which the v-sis gene was inserted. After purification by electrophoresis in a 0.5% low-melting temperature agarose gel, the fragment was ligated as described below.

A DNA fragment corresponding to the putative rPDGF B$_{c\text{-}sis}$ protein precursor amino terminal region was synthesized according to published procedures (McBride and Caruthers, *Tetrahedron Lett.* 24: 245 (1983)). This fragment, the sequence of which is shown in FIG. 8, corresponds to the region spanning nucleotide 111 to nucleotide 203 of the rPDGF B protein cDNA clone described by Josephs et al., Science 225: 636 (1984). A SalI site was added at the upstream end to permit ligation to the pDSVE vector. The SstI site at the downstream end occurs naturally at this position in both c-sis and v-sis.

Figure 9:
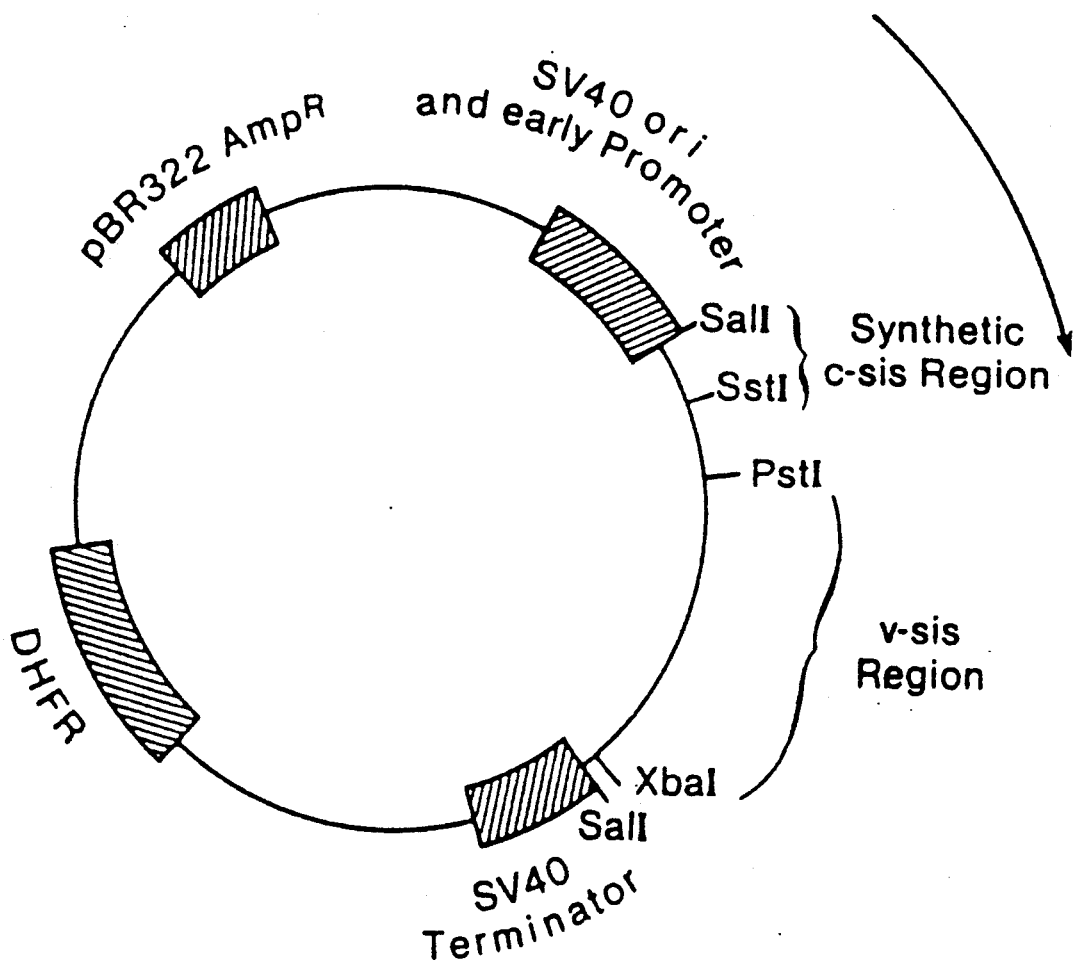
FIG. 9 is a schematic depiction of the plasmid pDSVE/cv-sis.

The final expression vector was assembled in a 3-way ligation reaction containing 100 ng of Sal I-cut pDSVE, 2.6 ng of the synthetic SalI/SstI c-sis fragment, and 25 ng of the SstI/SalI v-sis fragment. After overnight incubation at 14° C. in the presence of T4 DNA ligase, the reaction products were transformed into E. coli K12 strain DH1. Duplicate replica filters were made of ampicillin resistant colonies. One of the filters was hybridized to a radiolabeled v-sis probe as described above; the other was hybridized to radio-labeled synthetic SalI/SstI c-sis fragment. A clone which hybridized to both probes was grown in liquid culture, and the plasmid it harbored was isolated by standard procedures. Restriction mapping with XbaI, HindIII, EcoRI and PstI confirmed that this plasmid, named pDSVE/cv-sis, contained elements arranged as shown in FIG. 9. The amino acid sequence of the protein expected as the initial translation product of this gene is shown in FIG. 10.

EXAMPLE 3

Mammalian Cell Transformation; Clone Selection; and Gene Amplification

In order to achieve high level production of biologically active rPDGF B, the expression plasmids described in Example 2 were introduced into a mammalian cell line. The procedures used are essentially those described in PCT Patent Application No. US84/02021, 58-63, which is incorporated by reference herein.

CHO DHFR⁻ cells (DuX-811) cells described by Urlaub et. al., Proc. Natl. Acad. Sci. (U.S.A.) 77: 4461 (1980), lack the enzyme dihydrofolate reductase (DHFR) due to mutations in the structural genes and therefore require the presence of glycine, hypoxanthine, and thymidine in the culture media. Plasmids pDSVE/c-sis, pDSVE/v-sis or pDSVE/cv-sis were transfected along with carrier DNA into CHO DHFR⁻ cells growing in media containing hypoxanthine, thymidine, and glycine in 60 mm culture plates. The plasmid and carrier DNA mixture was transfected into CHO DHFR⁻ cells.

After three days, the cells were dispersed by typsinization into several 100 mm culture plates in media lacking hypoxanthine and thymidine. Only those cells which have stably transformed with the DHFR gene, and thereby the rPDGF B gene, survive in this media.

After 7-21 days, colonies of surviving cells became apparent. These transformant colonies, after dispersion by typsinization, may be continuously propagated as a mixed population in media lacking hypoxanthine and thymidine, creating new cell strains (e.g., CHO-pDSVE/v-sis, CHO-pDSVE/cv-sis). Alternatively, individual colonies may be trypsinized and transferred to the wells of microtiter dishes, creating new, clonal cell lines (e.g., CHO-pDSVE/c-sis). Cell lines CHO-pDSVE/v-sis, CHO-pDSVE/cv-sis and CHO-pDSVE/c-sis were respectively deposited on Mar. 13, 1987 with the American Type Culture Collection, 12301 Parklawn Drive, Rockville, Md. 20852, as ATCC Nos. CRL 9359, CRL 9360 and CRL 9358.

Culture fluids from the above cell strains, including those derived by growth of CHO-pDSVE/c-sis clones in microtiter wells, were tested in a bioassay and in a radioimmunoassay (RIA) as, described in Example 4, for the presence of rPDGF B. Representative 5 day culture fluids from CHO-pDSVE/v-sis and CHO-pDSVE/cv-sis cells contained approximately 100 to 200 ng/ml of rPDGF B as determined in both assays. Culture fluids from one of the CHO-pDSVE/c-sis clones, which clone was used in subsequent work, contained approximately 200 ng of rPDGF B per milliliter. Culture fluids from cells transformed only with pDSVE did not contain detectable amounts of rPDGF B.

The quantity of recombinant rPDGF B produced by the cell strains described above may be increased by gene amplification, yielding new cell strains of greater productivity. The enzyme dihydrofolate reductase, which is the product coded for by the DHFR gene, may be inhibited by the drug methotrexate (MTX). More specifically, cells propagated in media lacking hypoxanthine and thymidine are inhibited or killed by MTX. Under the appropriate conditions (e.g., minimal concentrations of MTX), cells resistant to and able to grow in MTX may be obtained. These cells are usually found to be resistant to MTX due to an amplification of the number of their DHFR genes, resulting in increased production of DHFR enzyme. The surviving cells may, in turn, be treated with increasing concentrations of MTX, resulting in cell strains containing even greater numbers of DHFR genes. "Passenger genes" (e.g., rPDGF B) carried on the expression vector along with the DHFR gene are frequently found also to be increased in their gene copy number.

Illustrative of this amplification system, cell strains CHO-pDSVE/c-sis, CHO-pDSVE/v-sis or CHO-pDSVE/cv-sis were subjected to increasing MTX concentrations (0 nM, 30 nM and 100 nM). Representative 5 day culture media samples from each amplification step of CHO-pDSVE/c-sis were assayed by RIA and determined to contain 0.2, 2.0 and 2.0 $\mu$g/ml, respectively, of rPDGF B. Representative 5 day culture media samples from each amplification step of CHO-pDSVE/v-sis and CHO-pDSVE/cv-sis contained rPDGF B at 0.15, 1.0 and 1.0 $\mu$g/ml, respectively. In these procedures, $1 \times 10^6$ cells were plated in 5 ml of media in 60 mm dishes. Twenty-four hours later the media were removed and replaced with 5 ml of serum-free media (high glucose DMEM supplemented with 0.1 mM non-essential amino acids and 2 mM L-glutamine). rPDGF B was allowed to accumulate for 5 days in the serum-free media. The media was collected for RIA assay and the cells were trypsinized and counted. The average RIA values of 2.0 $\mu$g/ml and 1.0 $\mu$g/ml for CHO-pDSVE/c-sis and CHO-pDSVE/v-sis (or CHO-pDSVE/v-sis) cells, respectively, grown in 30 nM MTX, provided actual yields of 10 $\mu$g/plate and 5 $\mu$g/plate. The number of cells per plate was $2.5 \times 10^6$. The effective production rates for these culture conditions were thus 0.8 and 0.4 $\mu$g/$10^6$ cells/24 hours.

The cells in the CHO-pDSVE/v-sis and CHO-pDSVE/cv-sis cultures described immediately above were a genetically heterogeneous population. Standard screening procedures were employed for these cells, as well as for pDSVE/v-sis cells, in order to isolate genetically homogeneous clones with the highest production capacity. See Section 1, Part 2, of "Points to Consider in the Characterization of Cell Lines Used to Produce Biologics", Jun. 1, 1984, Office of Biologics Research Review, Center for Drugs and Biologics, U.S. Food and Drug Administration.

The productivity of the rPDGF B producing CHO cell lines described above may be improved by appropriate cell culture techniques. The propagation of mammalian cells in culture generally requires the presence of serum in the growth media. A method for production of rPDGF B from CHO cells in media that does not contain serum is expected to greatly facilitate the purification of rPDGF B from the culture medium when standard protein purification techniques are used. The method described below is capable of economically producing rPDGF B in serum-free media in large quantities sufficient for production.

rPDGF B-producing CHO cells, grown in standard cell culture conditions, are used to seed spinner cell culture flasks. The cells are propagated as a suspension cell line in the spinner cell culture flask in media consisting of 50-50 mixture of high glucose DMEM and Ham's F12 (Gibco) supplemented with 5% fetal calf serum, 2 mM L-glutamine, 0.05 mM non-essential amino acids and the appropriate concentration of methotrexate. Suspension cell culture allows the rPDGF B-producing CHO cells to be expanded easily to large volumes.

The CHO cells, grown in suspension, are used to seed roller bottles at an initial seeding density of $1.5 \times 10^7$ viable cells per 850 cm$^2$ roller bottle in 200 ml of media. The cells are allowed to grow to confluency as an adherent monolayer over a three-day period. The medium used for this phase of the growth is the same as used for growth in suspension. At the end of the three-day growth period, the serum-containing media is removed and replaced with 100 ml of serum-free media; 50-50 mixture of high glucose DMEM and Ham's F12 supplemented with 0.05 mM non-essential amino acids and 2 mM L-glutamine. The roller bottles are returned to the roller bottle incubator for a period of 1-3 hours and the media again is removed and replaced with 100 ml of fresh serum-free media. The 1-3 hour incubation of the serum-free media reduced the concentration of contaminating serum proteins.

The roller bottles are returned to the incubator for seven days during which time rPDGF B accumulates in the serum-free culture media. At the end of the seven-day production phase, the conditioned media is removed and replaced with fresh serum-free medium for a second production cycle. Illustrative of this production system, a representative seven-day, serum-free medium sample contained rPDGF B$_{c\text{-}sis}$ at 1 µg/ml as judged by the RIA and mitogenesis assay. Based on an estimated cell density of 0.9 to $1.8 \times 10^5$ cells/cm$^2$, each 850 cm$^2$ roller bottle contained from 0.75 to $1.5 \times 10^8$ cells and thus the rate of production of rPDGF B$_{c\text{-}sis}$ in the 7-day, 100 ml culture was 0.10 to 0.19 µg/10$^6$ cells/24 hours.

When using a preferred method of rPDGF B purification involving affinity chromatography (described below in Examples 6 and 10), it was found that the presence of low levels of serum in the conditioned medium did not complicate purification. These low serum levels did, however, lead to increased levels of rPDGF B$_{c\text{-}sis}$ being secreted into the medium by CHO-pDSVE/c-sis or CHO-pDSVE/v-sis cells. Therefore, a procedure modified from the one described above for large scale tissue culture was adopted.

Cells are grown in spinner flasks and innoculated into roller bottles exactly as described above. After 3 days of growth to confluency, the medium is removed and replaced with 100 ml of the same medium containing 1% serum. The bottles are returned to the incubator and after 7 days the medium is removed. Another 100 ml may be added to the cells for another 7 day cycle of accumulation of rPDGF B in the medium. This cycle may be repeated several times before production levels fall off significantly. A representative 7-day sample contained 3 µg/ml of rPDGF B$_{c\text{-}sis}$.

The high levels of active rPDGF B produced by CHO cells containing a foreign rPDGF B gene were unexpected, being 20-100 fold higher than the levels reportedly produced by a variety of other cell types into which a rPDGF B gene had previously been introduced (Huang et al., *Cell* 39: 79 (1984); Johnsson et al., *Proc. Natl. Acad. Sci. U.S.A.* 82: 1721 (1985); Kelly et al., *EMBO J.* 4: 3399 (1985); or cells in which an endogenous PDGF B gene is expressed (Nilsson et al., *Proc. Natl. Acad. Sci. U.S.A.* 82: 4418 (1985); Martinet et al., *Nature* 319: 158 (1986); Goustin et al., *Cell* 41: 301 (1985); Rizzino et al., *Dev. Biol.* 110: 15 (1985); Westermark et al., *Proc. Natl. Acad Sci. U.S.A.*: 83: 7197 (1986); Fox and DiCorleto, *Proc. Natl. Acad. Sci. U.S.A.* 83: 4774 (1986); Heldin et al., *Nature* 319: 511 (1986). Contrary to previously reported results, the levels of PDGF produced according to the present invention are great enough to be practical and useful.

The levels of active rPDGF B secreted into the culture media by CHO and other vertebrate cells may also be increased by altering the amino acid sequence of the precursor protein which is "upstream" of or amino terminal to the mature, secreted form of the protein. For instance, the portion of the rPDGF B chain gene encoding the region of rPDGF B$_{c\text{-}sis}$ upstream of amino acid number 82 in FIG. 2 may be deleted and replaced with a DNA sequence coding for the amino terminal region of another protein, which protein is known to be secreted by CHO or other vertebrate cells in large quantity. More specifically, the upstream DNA sequence may be replaced with a DNA sequence coding for the amino terminal region of the protein erythropoeitin, which protein can be secreted from CHO cells in large quantity.

EXAMPLE 4

Analysis of PDGF-Related Proteins In CHO Cells and Conditioned Media

4(a) Mitogenesis Assay of Conditioned Media: rPDGF B samples were tested for biological activity in a mitogenic assay. NIH 3T3 cells were plated at a density of $3 \times 10^4$ cells per well in a 24-well plate (area approximately 2 cm$^2$), and allowed to grow to confluency at 37° C. in a cell growth medium consisting of Dulbecco's minimum essential medium ("DMEM"), supplemented with penicillin (100 units per ml) and streptomycin (100 µg per ml), and containing 10% heat-inactivated calf serum. At confluency, the medium was changed to the same supplemented DMEM containing 5% human platelet-poor plasma (Rutherford and Ross, *J. Cell Biology* 69: 196 (1976)). Forty-eight hours after media change, PDGF standards and assay samples were added to the wells and incubation at 37° C. continued for 18 hours. Media was removed, and the cells were labeled for exactly one hour at 37° C. in one ml of fresh supplemented DMEM containing 5% heat inactivated calf serum and 2µCi per ml of Me-$^3$H-thymidine (New England Nuclear, 20 Ci/m Mole). After one hour, the cells were chilled, medium was removed, and cell sheets were washed with cold phosphate-buffered saline (PBS), then with cold 5% Trichloracetic acid (TCA) which was allowed to stand for 5 minutes on ice. The TCA was removed, cells were washed once with fresh cold 5% TCA, the wash was aspirated off and cell sheets were dried. The contents of each well were dissolved in 1.0 ml of 0.25M sodium hydroxide, transferred to a glass vial containing 10 ml of Aquasol II ® scintillation cocktail (New England Nuclear Boston, Mass.), and counted in a Beckman liquid scintillation counter. A standard curve was constructed covering the concentration range of 2 to 120 ng per ml of PDGF, and PDGF activity of assay samples was calculated from the standard curve.

4(b) Radioimmunoassay utilizing PDGF from human platelets and anti-PDGF serum: The specific radioimmunoassay used to detect and quantitate rPDGF B employed PDGF purified from human platelets and rabbit polyclonal antisera raised against PDGF from the same source. Human platelet PDGF (0.5 µg) was iodinated using [$^{125}$I] Na and Iodo-Gen ™ (Pierce Chemical Co., Rockford, Ill.) by the procedure of Fraker and Speck, *Biochem. Biophys. Res. Commun.* 80: 849 (1978). [$^{125}$I]-PDGF (30,000 cpm) was incubated with an amount of antiserum which resulted in half-maximal precipitation of the labeled PDGF, in a 60 µl reaction containing RIA buffer (10 mM Tris-HCl, pH 8; 150 mM NaCl; 0.4% Nonidet ™ P-40 (Sigma, St. Louis, Mo.); and 0.1% BSA) for 16 hours at 4° C. A standard curve was generated by pre-incubation of the antiserum with varying amounts of unlabeled human platelet PDGF for 1 hour at room temperature, prior to addition of the $^{125}$I-PDGF. At the end of the reaction period, 50 µl of a washed, 10% suspension of killed *Staphylococcus aureus* (*S. aureus*) was added and the mixture was incubated for 45 minutes at room temperature. The *S. aureus*, along with bound antibody and antibody-antigen complexes, was pelleted by centrifugation for 2 min. in a Beckman Microfuge. The pellet was washed three times with RIA buffer and the precipitated radioactivity was determined in a gamma radiation counter. The amount of inhibition of the antibody $^{125}$I-PDGF reaction was plotted against the amount of platelet PDGF competitor added. The amount of PDGF immunoreactive material in unknown samples was assessed by comparison of its competitive activity to the standard curve.

4(c) Immunoprecipitation of in vivo labeled intracellular and secreted PDGF-related proteins: In order to determine the size of rPDGF B proteins synthesized in and secreted by CHO cells containing sis vectors, the cells were first incubated with $^{35}$S-cysteine for 20 hours to label cysteine-containing proteins. The label incorporated into proteins is believed to approach a steady state distribution during this time period. Labeled PDGF-related proteins were specifically detected by immunoprecipitation with antiserum to human platelet PDGF and analyzed by SDS-PAGE and flourography. CHO-pDSVE/c-sis, CHO-pDSVE/v-sis, CHO-pDSVE/cv-sis or CHO-pDSVE (as a control) cells were grown to approximately 80% confluency in 10 cm culture plates. The cells were washed twice with cysteine-deficient medium. Four milliliters of cysteine-deficient medium containing 0.625 mCi of $^{35}$S-cysteine was added to each plate. After incubation for 20 hours at 37° C., the media were collected and made 1 mM in PMSF and 0.025% in sodium azide to inhibit protease action and bacterial growth. The cells on each plate were lysed by addition of 1.4 ml of disruption buffer (0.025M Tris-HCl, pH 8.0; 0.05M NaCl; 0.5% sodium deoxycholate; 0.5% Nonidet ™ P-40; 1 mM PMSF). Insoluble material was removed by centrifugation for 1 min. in a Beckman Microfuge. Aliquots of media or cell extracts containing equal amounts of TCA-insoluble labeled material were pre-incubated with rabbit non-immune serum. Non-specifically-reacted proteins were removed by addition of Protein A-Sepharose (BioRad, Richmond, Calif.) and centrifugation as above. Anti-PDGF serum was added to each supernatant. After incubation at 4° C. for 16 hours, specifically-reacted proteins were removed by addition of Protein A-Sepharose ™ for 1 hour at room temperature, followed by centrifugation as above. The Protein A-Sepharose ™ /immune complexes were washed 6 times with RIA buffer. Bound immune complexes were disrupted and released from the protein A-Sepharose ™ by boiling in 1% SDS for 5 minutes. Each supernatant was split into two equal portions, and gel loading buffer (1% SDS, 20% glycerol, 0.1% bromophenol blue) either with or without reducing agent (3% 2-mercaptoethanol) was added to each aliquot. The samples were boiled again and then electrophoresed through an 18% SDS-polyacrylamide gel. The gels were treated with En$^3$Hance ™ (New England Nuclear, Boston, Mass.), dried, and exposed to X-ray film for 2-10 days.

The major stable intracellular form of rPDGF B in cells transformed by sis-containing vectors ran as a homogeneous band of 23 kd. After reduction, this form was converted to three smaller species of approximately 8.5 kd, 7.5 kd and 7 kd.

The major extracellular forms of rPDGF B secreted by these cells were heterogeneous. The two species with the greatest intensities on the autoradiograms had mobilities corresponding to 27.5 kd and 25 kd. A 30.5 kd species was somewhat less intense. A fourth species of much lower intensity was similar in size to the major intracellular form, i.e. 23 kd. The reduced forms of extracellular rPDGF B were also heterogeneous. The most intense band had a mobility corresponding to 13.5 kd. Somewhat less intense bands of 17 kd, 16 kd and 12 kd were also present. Much less intense bands of 8.5 kd, 7.5 kd and 7 kd were observed, similar to the sizes of bands observed in the reduced intracellular rPDGF B lanes. It should be noted that band intensities in these autoradiograms do not necessarily reflect the true distribution of mass between the different molecular forms, but rather are also dependent on the cysteine content of each species.

None of the species described above were observed in cell extracts or media from control CHO-pDSVE cells, nor were they observed after reaction with control non-immune serum. The sizes and heterogeneity of the observed rPDGF B proteins immunoprecipitated from cell products of CHO cells transformed with sis vectors are in general agreement with previous observations on PDGF purified from human platelets.

EXAMPLE 5

Generation of Antisera to a Chicken Growth Hormone/PDGF Fusion Protein

5(a) Construction of pCGP1 and transformation of *E. coli*: To provide a source of large quantities of antisera that would react with rPDGF B, thus facilitating analysis and purification, an expression plasmid was constructed for introduction into *E. coli*. The plasmid was designed to code for a fusion protein consisting of the amino terminal 120 amino acids of chicken growth hormone (CGH) (Souza et al., *J. Exp. Zoology* 232: 465 (1984)) and the carboxy terminal 136 amino acids of the protein encoded by the v-sis gene. The complete sequence of the resulting protein, called CGP1 are shown in FIG. 11.

Two micrograms of M13mp18/v-sis(Kpn-Xba) RF DNA was restricted with BglII and BamHI. The 760 base pair fragment spanning the region between the BglII site at position 4061 of SSV (Devare et al., ibid., numbering system) and the BamHI site in the polylinker region of M13mp18 was purified on a low-melting temperature agarose gel. Seventy-five nanograms of the fragment were ligated to 90 ng of pCGHT1/CFM414 DNA (Souza et al., ibid.) that had been restricted with BamHI which cuts after amino acid number 120 of the CGH gene. The ligated DNA was transformed into *E. coli* K12 strain JM103.

Ampicillin-resistant colonies containing v-sis were identified by hybridization to a v-sis probe. Plasmid DNA was isolated from several such colonies and analyzed by restriction mapping with XbaI, BamHI and EcoRI. One clone, called pCGP1, had v-sis DNA inserted in the correct orientation for expression and was selected for further use.

5(b) Purification of CGP1 fusion protein: pCGP1 DNA was transformed into the *E. coli* strain K12 for expression. Cells of *E. Coli* K12 strain AM7 transformed with pCGP1 were deposited on Mar. 13, 1987 with the American Type Culture Collection, 12301 Parklawn Drive, Rockville, Md. 20852 as Deposit No. 67352. A 20-milliliter culture was grown overnight at 28° C. in Luria broth. One milliliter of this culture was used to innoculate one liter of Luria broth, and the larger culture was incubated at 28° C. on a rotary platform. Absorbance of the culture was monitored and when the absorbance at 600 nm was 0.5, the culture was shifted to 37° for 13.5 hours to induce expression of the fusion protein. The cells were pelleted by centrifugation and resuspended in 12 ml of 10 mM Tris-HCl (pH 7.5) and 1 mM EDTA. The cells were broken in a French pressure chamber and insoluble material was pelleted by low speed centrifugation.

Analysis by SDS-PAGE revealed a protein in the pelleted fraction of approximately 28 kd, which protein was not present in uninduced cells or in cells transformed with the vector alone. The protein was approximately 60% pure at this stage. The insoluble pellet was suspended in 20 ml of 20 mM Tris-HCl (pH 7.5), 5 mM EDTA, and 0.2 mg/ml lysozyme, and incubated for 30 minutes at room temperature. Nonidet TM P-40 was added to a concentration of 0.5%, and incubation was continued for another 30 min. Insoluble material was pelleted by centrifugation (5 min.; 10,000 X g), and the pellet was washed with 10 ml of water. Following centrifugation, the pellet was stirred with 4 ml of 50 mM Tris-HCl (pH 8.5), 5% ethanol, 1% sodium laurate for 30 minutes at room temperature. Following centrifugation as above the sodium laurate wash was repeated. The final pellet was dissolved in 4 ml of 1% SDS and 50 mM Tris-HCl (pH 7.4) by stirring overnight at room temperature. This preparation was judged to be approximately 80% pure by SDS-PAGE analysis.

5(c) Immunization of rabbits, production of polyvalent sera to rPDGF B fusion protein CGP1 and analysis of antisera: Rabbits were injected with CGP1 and bled according to the following schedule: On day O, a preimmune bleed was taken, and each rabbit was injected intradermally in multiple sites on the back with a total of 250 µg CGP1 in 1.0 ml of a mixture containing 50% emulsified BACTO-Freunds complete adjuvant H37 Ra (DIFCO 3113-60), as available from DIFCO, Detroit, Mich. in PBS. Fourteen days later, the rabbits were intradermally injected with 250 µg of CGP1 mixed with 50% Freunds incomplete adjuvant (DIFCO, BACTO 0639-60-6), as before. A second, identical booster injection was done on day 30, and on day 42 the rabbits were test bled. The resulting sera were tested for the production of anti-CGP1 antibodies.

Thereafter, those rabbits which tested positive for CGP1 antibodies were injected every 30 days as above, with 250 µg of CGP1 protein in 50% Freunds incomplete adjuvant, one-half of the dose being administered intradermally and one-half intraperitoneally. The rabbits were bled each time on days 14 and 21 after the injection. The resulting sera were tested for anti-CGP1 activity in an ELISA-plate binding assay. Ninety-six-well Immulon II TM wells (Dynatech Laboratories, Inc.) were coated with CGP1 fusion protein by incubating the wells for 16 hours at room temperature with 50 µl each of a mixture containing 5 µg/ml of CGP1 protein in a carbonate-bicarbonate buffer (0.015M $Na_2CO_3$ and 0.035M $Na_2C HO_3$ at pH 9.5). The mixture was removed, and the wells were blocked with 200 µl of 5% bovine serum albumin (BSA) in PBS for one hour at room temperature. The blocking agent was removed, and dilutions of the rabbit sera, both preimmune and immune were made in PBS and 1% BSA, and applied to the wells, 50 µl each.

After incubation for 3 hours at room temperature, the solutions were removed, and wells were washed three times with PBS. Bound rabbit antibody was detected by incubating each well for one hour with 50 µl of PBS/0.1% BSA containing $1 \times 10^5$ cpm of $^{125}I$-protein A (New England Nuclear, catalogue no. NEX146L). The radioactive solution was removed, and each well washed five times with PBS. Individual wells were separated and counted in the Beckman 5000 gamma counter.

Activity curves were constructed by plotting rabbit serum dilution ($10^{-1}$ to $10^5$) against counts per minute of bound $^{125}I$-protein-A, and the titer of each serum was determined to be the reciprocal of the dilution at which 50% of the maximum count was bound. Two of three rabbits were strongly positive for antibodies to CGP1 protein (#304 and #305), producing titers ranging from $5.6 \times 10^3$ and $1.5 \times 10^3$ initially to $2.6 \times 10^4$ and $4 \times 10^3$, respectively.

EXAMPLE 6

Construction of Anti-CGP1 Agarose Affinity Column and Use for Purification of rPDGF B from Conditioned Media 6(a) Immunoglobulin purification and construction of agarose affinity matrix: Ten milliliters of serum from rabbit #304 (anti-CGP1 titer of $> 10^4$) were centrifuged at 40,000 X g for 20 minutes. The clear supernatant was applied to the top of a $1.5 \times 6$ cm column of protein A-agarose, which was previously equilibrated with 0.02M sodium phosphate (pH 7.4), 0.14M sodium chloride, 0.02% sodium azide (PBS). The serum was allowed to run into the column, and the column was washed with PBS until the U.V. absorbance of the eluate at 280 nm was less than 0.02 units.

Immunoglobulin absorbed to the column was eluted with 0.58% acetic acid in 0.15M sodium chloride and was located in resulting fractions by U.V. absorbance. The fractions containing immunoglobulin were neutralized with 1.0M Tris buffer (pH 8.0). After dialysis against 3 changes of 4 liters of 0.1M sodium bicarbonate and 0.5M sodium chloride (pH 8.5) at 4° C., immunoglobulin concentration was determined by U.V. absorbance at 280 nM using an extinction coefficient of 1.46. The yield of rabbit immunoglobulin was 42.9 mg.

Three grams of cyanogen bromide-activated Sepharose TM 4B (Pharmacia Fine Chemicals, Uppsala, Sweden) was swelled in 0.001M HCl and washed on a glass funnel with 600 ml of the same solution. The wet gel was transferred to a 50 ml centrifuge tube and washed with 20 ml of coupling buffer (0.1M sodium bicarbonate and 0.5M sodium chloride at pH 8.5). After a 4 minute centrifugation at 600 x g, the supernatant fluid was removed and the 42.9 mg of rabbit immunoglobulin in 9.7 ml of coupling buffer was added to the Sepharose TM 4B. The mixture was tumbled end over end at 4° C. overnight, centrifuged as above, and the supernatant tested for the presence of residual immunoglobulin. Less than 0.3% of original immunoglobulin remained in the supernatant. Thus the efficiency of coupling was better than 99.7%.

The immunoglobulin-coupled Sepharose TM 4B was washed with 4 cycles of 0.1M sodium acetate, (pH 4.0), and 0.5M sodium chloride, followed by coupling buffer. The gel was equilibrated with buffer E (0.0026M KCl, 0.1369M NaCl, 0.0014M $KH_2PO_4$, and 0.008M $Na_2HPO_4$), poured into a 1.5×10 cm glass column, and washed at 4° C. with 100 ml of buffer E.

6(b) Affinity Purification of rPDGF B from Conditioned Media: Culture fluids, harvested after 4-7 days from roller bottle cultures of CHO-pDSVE/c-sis, CHO-pDSVE/v-sis, or CHO-pDSVE/cv-sis cells were centrifuged at 10,000 X g for 20 minutes, and the supernatant fluid passed through a 0.45μ filter. One hundred to 400 ml of filtered medium was adsorbed to a 10 ml anti-CGPl-Sepharose affinity column at a flow rate of 30 to 40 ml/hr, at 4° C. The column was washed sequentially with 20 column volumes of buffer F (0.5M NaCl, 0.025M Tris-HCl, pH 7.5, and 0.1% Nonidet TM P-40 and at least 5 column volumes of buffer G (0.15M NaCl, 0.01% Nonidet TM P-40). Bound rPDGF B was eluted with buffer H (0.2M acetic acid, 0.15M NaCl and 0.01% NP40) at a rate of 30 ml/hour. One milliliter fractions were collected, and rPDGF B containing fractions were located by testing 50 1 aliquots in the Bio-Rad protein assay (Bio-Rad, Richmond, Calif.), and by immunological assay in a dot immunobinding assay employing rabbit anti-CGPl antiserum as described below. Protein-containing fractions were pooled, dialyzed against 0.1M acetic acid and 0.01% Nonidet TM P-40 at 4° C., and then lyophilized.

6(c) Characterization of rPDGF B from rabbit immunoglobulin affinity column by dot immunobinding assay: Fractions recovered from the anti-CGPl-agarose affinity column were assayed for rPDGF B by a dot immunobinding assay in accordance with the procedures described by (Towbind et al., *J. Immunol. Methods* 72: 313 (1984)). Twenty-five to 100 μl of test fractions were adsorbed to nitrocellulose paper (0.2μ, #BA-83, Schleicher and Schuell, Keene, N. H.), in a 96-well manifold apparatus (SRC-96, Schleicher and Schuell). Varying amounts of CHO-pDSVE/v-sis media containing 10 to 400 ng of rPDGF $B_{v-sis}$, were absorbed separately and served as standards. The nitrocellulose paper was "blocked" by shaking in a solution of 10% dried, non-fat milk powder (Carnation, Los Angeles, Calif.) in PBS (pH 7.4) (0.15M NaCl, 10 mM $Na_2HPO_4$ (pH 7.4), incubated with a 1:50 dilution of rabbit anti-CGPl serum in PBS-1% dried milk powder, and washed three times with PBS containing 0.025% Tween TM 20. The detection of bound antibody was carried out with a VectaStain TM Kit, according to the manufacturer's instructions (Vector Laboratories, Burlingame, Calif.). Approximate rPDGF B concentrations in column fractions were estimated by color intensity of column fraction "dots" by comparison with standard "dots".

6(d) Characterization of rPDGF B from rabbit immunoglobulin affinity column by SDS-PAGE Analysis, Coomassie Blue, Silver Stain and Immunoblotting: Lyophilized rPDGF B fractions from the rabbit immunoglobulin affinity column were reconstituted in 10 mM acetic acid. Aliquots (0.2 to 2 μg) were loaded (either non-reduced or reduced with 5% 2-mercaptoethanol) into wells of either 15% or 18% polyacrylamide gels, 1.5 mm thick. Electophoresis was performed in Tris-glycine buffer (0.025M Tris, 0.192M glycine) containing 0.1% SDS, at 80-90 volts for 10-12 hours. Protein bands were visualized by development with Coomassie Blue stain or with silver stain (RAPID-Ag-STAIN, ICN Radiochemicals, Irvine Calif.), or protein was transferred from the developed gel to nitrocellulose paper (BA83, Schleicher and Scheull) by an electrophoretic transfer technique (BioRad Trans-Blot Cell, catalogue no. 170-3910) employing electrical current to drive the resolved bands from the gel onto the surface of the paper. The transfer was carried out in a buffer containing 0.15M glycine, 0.02M Tris base and 20% methanol (vol/vol), for 6 h at 60 V at room temperature. Coomassie Blue and silver-stained gels showed two major protein bands occurring in the area of a 25,400 mw marker for unreduced samples, and two bands close to a 14,400 mw marker for reduced samples. From the silver-stained gels, the rPDGF B was estimated to be more than 95% pure. Nitrocellulose blots were blocked with 10% goat serum and 2% BSA in PBS for 1 hour, incubated with the primary antibody for 2 to 3 hours, washed with KP (Kirkegaard and Perry, Gaithersburg, Md.) wash solution, incubated with secondary biotinylated goat anti-rabbit serum in PBS for 1.5 hours, and the antibody detection carried out using a VectaStain TM kit as above (see Example 6(c)). The primary antibody employed for the immunoblot was rabbit anti-CGPl serum, (#305) diluted 1:50.

Two major bands were visible on the blot from non-reduced rPDGF $B_{v-sis}$, at approximately 26,000 mw and 30,000 mw, based on prestained molecular weight markers run on the same gel and transferred to nitrocellulose. Less distinct rPDGF B-specific bands were visible at slightly higher molecular weights. In the blot from the reduced gel, two major rPDGF B-specific bands were detected between the 14,400 MW marker and the 18,300 MW marker. Additional, fainter bands were observed at molecular weights slightly less than 14,400 and at approximately 18,000.

EXAMPLE 7

Generation of Polyclonal and Monoclonal Antibodies to Purified rPDGF $B_{v-sis}$ 7(a) Immunization of rabbits and analysis of polyclonal antisera: Rabbits were immunized with rPDGF $B_{v-sis}$ (purified as described in Example 6) essentially as described for the CGP1 fusion protein in Example 5(c). Sera were titered as described in Example 5(c), using rPDGF $B_{v-sis}$ bound to the microtiter plate wells; generally, the titers were $>1 \times 10^4$.

These antisera were capable of specifically detecting as little as 1 ng of rPDGF B or 5 ng of PDGF purified from human platelets in a dot immunobinding assay (as described in Example 6(c)), at a dilution of 1:100. The antisera also specifically reacted with human platelet PDGF radioiodinated as described in Example 4(b), or rPDGF B radioiodinated by the Bolton-Hunter technique (Bolton et al., *Biochem. J.* 133: 529 (1973)), in a radioimmunoassay performed as described in Example 4(b).

7(b) Development of monoclonal antibodies: Immunization of mice and assay of sera. Five female mice, of strain Balb/c, (Jackson Laboratories, Ann Arbor, Me.) were each injected initially with 10 μg of rPDGF $B_{v-sis}$ purified as described in Example 6, in approximately 0.3 ml of a solution consisting of 0.15 ml of PBS [0.15m NaCl and 0.01M $Na_2HPO_4$ (pH 7.4)] emulsified by sonication with 0.15 ml Freunds complete adjuvant (Calbiochem-Behring modification, Calbiochem-Behring Corporation, La Jolla, Calif.). The mice received multiple subcutaneous injections on the back. Ten days later, each mouse received a booster immunization intraperitoneally, which immunization consisted of 10 μg rPDGF $B_{v-sis}$ in 0.3 ml of PBS emulsified in MPL/TDM special emulsion R-700 (RIBI Immunochemical Research, Inc., Hamilton, Mont.). The mice received 0.15 ml in multiple sites on the back, as before, and 0.15 ml intraperitoneally. Twenty days later, the mice were bled and sera were assayed for antibodies to rPDGF $B_{v-sis}$.

A plate binding immunoassay was utilized to test the mouse sera. rPDGF $B_{v-sis}$, (700 μg/ml) in 0.035M $NaHCO_3$ and 0.015M $Na_2CO_3$ was bound to the wells of a serological 96-well plate by incubating 50 μl of antigen solution overnight at room temperature. Removal of non-bound antigen was followed by blocking unbound sites with 250 μl per well of PBS containing 5% bovine serum albumin for one hour at room temperature. Fifty microliters of mouse sera dilutions, from $10^{-1}$ to $10^{-5}$ in PBS, were added to the antigen-containing, blocked wells, incubated at room temperature for three hours and removed. The wells were then washed three times with KP wash solution. Each well received 50 μl PBS containing $1 \times 10^5$ cpm $^{125}$I-rabbit antimouse immunoglobulin G (IgG) (NEX 1610, New England Nuclear) with 0.1% bovine serum albumin. Wells were incubated for 90 minutes, washed five times with KP wash solution and counted in a Beckman 5500 gamma counter. Three mice were producing antibodies to rPDGF $B_{v-sis}$ with titers of greater than or equal to $10^3$. These three were given two more booster immunizations, identical to the first booster one week after the bleed and ten days after the bleed.

7(c) Development of Monoclonal Antibodies: Generation and Screening of Hybridomas: Three days following the final booster immunization with rPDGF $B_{v-sis}$, the three mice were killed by cervical dislocation and rinsed with 70% ethanol. Spleens were removed asepticaly and placed in petri dishes (on ice) containing Dulbecco's Modified Eagle's Medium (Gibco) with pencillin G and streptomycin at 200 units and 200 μg per ml, respectively. The spleens were trimmed of fat and connective tissue, passed through two rinses in fresh media (as above) and placed in a sterile stomacher bag with 10 ml of the same medium. Disruption of the spleens in the stomacher apparatus (Stomacher Lab-Blender 80, Seward Laboratories, London, England) for 90 seconds was followed by filtration through four layers of sterile gauze, and the resulting spleen cells were pelleted by centrifugation for 10 minutes at 1000 rpm in an IEC-HN SII centrifuge. The cell pellet was washed twice with media (as above) containing penicillin-streptomycin and once with media containing no antibiotics. The cell pellet was resuspended in fresh medium and the cell concentration was determined by counting in a hemocytometer in the presence of 0.2% trypan blue.

Mouse myeloma cells SP 2/0, derived from Balb/c strain, were grown in HB101 medium (NC-200, New England Nuclear Research Products) containing 1% heat-inactivated fetal bovine serum (FBS). The cells were pelleted by centrifugation at 1000 rpm for 10 minutes, as for the spleen cells, and washed with Dulbecco's modified Eagle's Medium (DMEM) containing no antibiotic. The cell concentration was determined by counting in a hemocytometer in 0.2% trypan blue after resuspension in the same medium.

Spleen and SP 2/0 cells were combined in a ratio of 3:1 and centrifuged at 1000 rpm for 10 minutes as above. The supernatant fluid was aspirated away and cell fusion was conducted at 37° C. using polyethylene glycol (PEG) 1500, molecular weight 500–600. This procedure was carried out with constant gentle stirring by addition of the following, at the times indicated: 1.0 ml of 50% PEG in DMEM added over one minute, with one minute stirring; 1.0 ml DMEM containing 10% fetal bovine serum (FBS) over one minute; 1.0 ml of DMEM containing 10% FBS added over one minute; and 8 ml DMEM containing 10% FBS added over 2 minutes.

The resulting fused cells were centrifuged at 1000 rpm for 10 minutes as above, resuspended in approximately 45 ml of DMEM containing 10% FBS and also containing pencillin G and streptomycin at 100 units and 100 μg per ml, respectively. The cells were plated at 0.1 ml per well in 96-well plates previously equilibrated in 9% $CO_2$. Plates were incubated at 37° C. in 9% $CO_2$.

On day 2 each well received 0.1 ml of HAT medium (13.6 μg/ml hypoxanthine, 0.176 μg/ml aminopterin and 3.88 μg/ml thymidine) in DMEM containing 10% FBS. This medium selectively allows spleen cell-SP 2/0 hybrids to survive, screening out unfused SP 2/0 cells or those fused to other SP 2/0 cells. Unfused primary spleen cells from adult mice will not survive in culture for more than a few days.

On days 3, 4, 6, 9 and 12, 0.1 ml of medium was removed from each well, and 0.1 ml of fresh HAT in DMEM containing 10% FBS was added. On days 15, 19, 23 and 27, 0.1 ml of medium was removed from each well, and was replaced with 0.1 ml of DMEM containing 10% FBS and only hypoxanthine and thymidine in the same concentration as above. On day 18 culture supernatants from all wells were screened by ELISA assay for detection of antibody specific for rPDGF B.

An enzyme-linked immunosorbent assay (ELISA) was utilized for the detection of hybridomas producing antibodies to rPDGF $B_{v-sis}$. Wells of 96-well plates were coated overnight at room temperature with 50 μl of carbonate-bicarbonate solution, as in Example 5(c), containing 0.7 μg/ml of rPDGF $B_{v-sis}$. Antigen was removed and the wells were blocked for 1 hour at room temperature with 200 μl of 5% BSA in PBS.

Fifty microliter aliquots of culture fluid from each hybridoma well were incubated in the rPDGF $B_{v\text{-}sis}$ coated wells at room temperature for 3 hours, removed, and the wells were washed once with PBS containing 0.025% Tween TM 20 (wash solution). Horseradish peroxidase-labeled goat-antimouse IgG (Boehringer-Mannheim Biochemicals, Indianapolis, Ind.) was diluted 1:300 with PBS and 50 μl were incubated in each well for 2 hours at room temperature. Wells were washed five times with wash solution, flicked dry, and the color reaction developed with 100 μl of ABTS color reagent (Kirkegaard and Perry Laboratories, Gaithersburg, Md.). The wells were scanned at 414 nm employing a Titertek Multiscan (Flow Laboratories, Springfield, Va.).

Of the 432 master plate wells screened, 173 were significantly positive for reaction with rPDGF $B_{v\text{-}sis}$. Of the positives, cells from 22 wells were selected for further expansion and cloning. Cells from each of the selected wells were diluted into 3×96 wells each, giving rise to individual clones, or in some cases, a small number of clones per well. After 17 days of further culture in DMEM culture medium containing 10% FBS, culture fluids from all wells containing one or more cell clones were tested by ELISA assay as described above. Anti-rPDGF $B_{v\text{-}sis}$ antibody was detected in some wells of plates representing 15 of the 22 original master plate wells, and corresponding cells were subjected to further cloning. Of these 15, the cells corresponding to wells with highest titer were selected to be recloned to give single-cell clones.

From a further ELISA assay of the single cell clones, 12 cultures were selected as producing the highest titers, representing 12 different wells of the original master plates. Each of the selected hybridoma cultures was expanded for further testing and ascites production in mice.

7(d) Production and Purification of High-Titer Monoclonal Antibodies: Selected positive single cell hybridoma clones were expanded in culture, cells were harvested, centrifuged at 700 rpm in an IEC-HNSII centrifuge for 5 minutes, washed once with DMEM (no serum) and once with PBS. Washed hybridoma cells were suspended at $2 \times 10^7$ cells/ml in PBS, and $5 \times 10^6$ cells were injected intraperitoneally into female Balb/c mice (Jackson Laboratories, Bar Harbor, Me.) 6 to 8 weeks of age or into female CDFI hybrid mice from the same source.

Ascites fluid developed in injected mice at 8 to 14 days. The ascites fluid was harvested, centrifuged at 2000 rpm (IEC-HN-SII) for 10 minutes, and the clear supernatant fluid was utilized further as a source of monoclonal antibody.

Reactivity and titer of the monoclonal antibodies in the ascites fluids were assayed against rPDGF $B_{v\text{-}sis}$ by a plate binding assay essentially as described in Example 5(c) wherein rPDGF $B_{v\text{-}sis}$ was coated at 0.7 μg/ml, and serial ten-fold dilutions of ascites fluids were made in PBS containing 1% BSA. In this case, the murine monoclonal antibody was detected with $^{125}$I-Rabbit anti-mouse IgG antibody (NEX 161, New England Nuclear, Boston, Mass.) approximately $10^5$ cpm (Beckman 5500 gamma counter) per well. Titers of individual ascites fluids were calculated as the reciprocal of the dilution at which 50% of maximum binding occurred. Titers of ascites from 12 different monoclonal antibody-producing clones ranged from $1.5 \times 10^4$ to $7.5 \times 10^5$. Results are given in Table 1.

Purification of immunoglobulin from hybridoma ascites fluids was carried out by a two step purification scheme in which clarified ascites fluid was first passed through a Cm-Affi-Gel Blue Column (Bio-Rad), which binds primarily albumin and proteases but which allows immunoglobulins to pass through. This step was carried out with PBS as a washing buffer. Unadsorbed material was diluted with an equal volume of binding buffer (MAPS II, Bio-Rad) and adsorbed to a 1.5×6 cm Affi-Gel Protein A column (MAPS II, Bio-Rad) as described in Example 7(b). Resulting purified immunoglobulin fractions were dialyzed against PBS, and immunoglobulin concentrations were calculated from the absorbance at 280 nm, using an extinction coefficient of 1.46.

7(e) Characterization of monoclonal antibodies to rPDGF $B_{v\text{-}sis}$: Reaction with PDGF from human platelets: Individual monoclonal antibodies were assayed for their ability to recognize natural human platelet PDGF, utilizing a modification of the dot immunobinding assay (as described in Example 6(c)). Nitrocellulose paper squares (2.5 cm$^2$) were divided into 5 sections. In a defined pattern, each section was dotted with 1 μl of PBS solution containing one of the following: 10 ng rPDGF $B_{v\text{-}sis}$, 50 ng rPDGF $B_{v\text{-}sis}$, 10 ng platelet PDGF, 50 ng platelet PDGF or 50 ng of a non-related growth factor (EGF). The nitrocellulose blots were blocked by shaking with 10% horse serum, 2% BSA in PBS for one hour. The blocking solution was removed and the blot was reacted with one of 9 primary antibodies (8 rPDGF B monoclonals and 1 rabbit anti-platelet PDGF serum) for 3 hours and washed with KP wash solution. Bound primary antibody was detected by reaction with a secondary biotinylated horse anti-mouse IgG antibody, an avidin-horseradish peroxidase complex, and substrate color reagent HRP (BioRad 1.70-6534) containing 4-chloro-1-napthol; 60 mg of the last reagent was dissolved in 20 ml methanol, diluted into 100 ml TBS (0.2M NaCl, 0.05M Tris, pH 7.4) containing 60 μl of 30% hydrogen peroxide.

All eight monoclonal antibodies tested gave distinct reactions with both 10 and 50 ng of rPDGF $B_{v\text{-}sis}$. Six of the eight monoclonal antibodies (designated as numbers 162, 30, 20, 219, 191 and 52) reacted with 50 ng of platelet PDGF and one of these six reacted with 10 ng of platelet PDGF. Rabbit anti-platelet PDGF serum readily detected 10 ng of platelet-derived material. No reaction was apparent between any of the antibodies and the non-related protein growth factor.

Monoclonal antibody reactivity and specificity were also assessed in a Western immunoblot format as in Example 6(c) in which both reduced and non-reduced rPDGF $B_{v\text{-}sis}$ were tested. All twelve monoclonal antibodies readily detected the two major bands of non-reduced rPDGF $B_{v\text{-}sis}$ which migrated as 25,000 and 27,500 mw proteins in 15% non-reducing polyacrylamide gels, but none gave any visible reaction with reduced rPDGF B run on identical gels and transferred to nitrocellulose under identical conditions.

7(f) Characterization of monoclonal antibodies to rPDGF $B_{v\text{-}sis}$: Subtype analysis: The twelve selected monoclonal antibody clones were screened for their immunoglobulin subtype utilizing a mouse immunoglobulin subtype identification kit (catalogue no. 100 036, Boehringer-Mannheim, Indianapolis, Ind.). For each antibody tested, 9 wells of a 96-well tray were coated with 50 μl of a solution of 0.7 μg/ml rPDGF $B_{v-sis}$ in carbonate-bicarbonate buffer (as in Example 5) overnight. Remaining protein binding sites were blocked by incubation with 200 μl per well of 2% BSA in PBS for 2 hours at room temperature. To each well was added 50 μl of one of the monoclonal antibodies (approximately 0.5 μg of immunoglobulin), and incubation was continued for 3 hours at room temperature. The wells were washed with 200 μl washing buffer (10 mM Tris-HCl, pH 7.0; 0.05% Tween 20; 0.01% thimerisol) four times. Fifty microliters of each rabbit anti-mouse subclass specific immunoglobulin, reconstituted according to the manufacturer's instructions, was added to each of 8 wells per monoclonal antibody. Normal rabbit serum was added to a ninth well as control. Incubation for 2 hours at room temperature was followed by 4 washes as described above. 50 μl of peroxidase-labeled goat anti-rabbit IgG was added to each well with incubation for one hour at room temperature. After four more washes, color was developed by addition to each well of 100 μl freshly-prepared ABTS-$H_2O_2$ (1 mM ABTS in 0.03% $H_2O_2$). After incubation for 20 to 30 minutes, the color reaction was stopped (by 2.5% SDS) and color was quantitated by reading the plates in a Titertek Multiscan at 414 nm. The results are given in Table 1. Six hybridomas produced antibodies of the $IgG_1$ subtype, while three were classified as IgG2a and three were classified as IgG2b. In Table 1, antibody titer is given as the reciprocal of the dilution at which 50% of the maximum cpm is bound.

TABLE 1

| Monoclonal Antibody No. | Ig Sub-type | Antibody titer Ascites fluid | Recognition of A and/or B chain |
|---|---|---|---|
| 30 | $IgG_1$ | $1 \times 10^5$ | B |
| 133 | $IgG_{2a}$ | $9 \times 10^4$ | A & B |
| 155 | $IgG_{2a}$ | $8 \times 10^4$ | B |
| 232 | $IgG_{2b}$ | $4 \times 10^4$ | B |
| 52 | $IgG_1$ | $1.5 \times 10^4$ | B |
| 191 | $IgG_1$ | $1.5 \times 10^4$ | B |
| 20 | $IgG_1$ | $7.5 \times 10^4$ | B |
| 116 | $IgG_{2a}$ | $5 \times 10^4$ | B |
| 198 | $IgG_1$ | $7.5 \times 10^5$ | A & B |
| 162 | $IgG_1$ | $2.5 \times 10^4$ | A & B |
| 296 | $IgG_1$ | $6.5 \times 10^4$ | B |
| 219 | $IgG_{2b}$ | $2 \times 10^5$ | A & B |

7(g) Assay for neutralization of rPDGF $B_{v-sis}$ mitogenic activity: Monoclonal antibodies raised against rPDGF $B_{v-sis}$ were tested for the ability to neutralize the biological activity of rPDGF $B_{v-sis}$ in the mitogenesis assay for $^3H$-thymidine incorporation into murine NIH cells (as in Example 4). The immunoglobulin fraction from each of 6 ascites fluids, generated from 6 different hybridomas, was isolated by chromatography on a protein A-agarose column. The specific technique utilized was Bio-Rad's Affi-Gel Protein A MAPS II monoclonal antibody purification system. Two to five milliliter of clarified ascites fluid diluted 1:1 with binding buffer were adsorbed to a 5 ml column of purified protein A coupled to cross-linked agarose beads and pre-equilibrated with binding buffer provided by the manufacturer. After washing non-bound protein from the column with approximately 10 volumes of binding buffer, the bound immunoglobulin was eluted at pH 3, and the immunoglobulin fractions located by reading absorbance at 280 nm. Pooled fractions were neutralized with 3.0M Tris buffer (pH 9.5) and dialyzed against PBS. The immunoglobulin concentration was determined.

Serial dilutions of the purified monoclonal immunoglobulins were incubated with 8 ng of rPDGF $B_{v-sis}$ at 4° C. for 12 hours before applying each mixture to an individual bioassay well in the standard mitogenesis assay as described in Example 4. Antibodies from clone #162 were most effective in neutralizing the effect of rPDGF B on $^3H$-thymidine uptake, giving activity at less than 100 ng. Anti-bodies from clones 155, 133, 52 and 30 were intermediate in activity, but still neutralizing. Clone 232 showed no activity.

7(h) SDS-PAGE analysis of purified monoclonal antibodies: The immunoglobulin fractions of the monoclonal antibody ascites fluids were analyzed by SDS-PAGE on 12.5% gels. Approximately 2 μg of each immunoglobulin was run in comparison with the same quantity of immunoglobulin from unfractionated ascites. All samples were reduced by treatment at 100° C. for 5 minutes in 5% 2-mercaptoethanol before applying to the gel. Electrophoresis and silver-staining of gels were performed as described in Section 6(d). The stained gels revealed a high degree of purity of all immunoglobulin fractions and the presence of amounts of heavy- and light-chain IgG expected from the amounts loaded. Each immunoglobulin sample assayed contained heavy- and light-chain components which migrated on the gel to the expected molecular weight positions of 50,000 and 25,000 respectively.

EXAMPLE 8

Development of Immunoassays for PDGF Utilizing Monoclonal and Polyclonal Antibodies to rPDGF $B_{v-sis}$ Sensitive and very specific immunoassays may employ monoclonal and polyclonal antibodies to rPDGF B according to the present invention in a variety of combinations and variations, and may utilize a variety of detection schemes. The present invention comprehends all of the possible combinations and variations that utilize monoclonal antibodies directed against native, non-reduced, dimeric PDGF according to the present invention, and is not limited to the specific example described here. Such assays may be useful for the diagnosis and prediction of prognosis in certain pathological conditions, e.g., some forms of cancer.

Purified monoclonal antibody 162 (50 μl) was adsorbed to the wells of Nunc 96-well microtiter plates at 5 μg/ml in 0.05M sodium carbonate (pH 9.2) in an overnight incubation at room temperature. The solution was aspirated and the remaining protein adsorption sites were blocked with 150 μl of 2% gelatin for 45 minutes at room temperature. The solution was aspirated and the wells were rinsed once with PBS containing 0.025% Tween TM 80. Fifty microliters of antigen in PBS containing 0.025% Tween TM 80 and 0.2% gelatin were added to each well, before incubation for 1.5 to 2 hours at room temperature.

The antigen solution was removed and the wells were washed once with PBS containing 0.025% Tween TM 80. A rabbit polyclonal antiserum raised against rPDGF B was diluted 1:1000 in PBS containing 0.025% Tween TM 80 and 0.2% gelatin, and 50 μl was added to each well. After incubation at room temperature for 1 to 1.5 hours, the solution was removed. The wells were washed once with PBS containing 0.025% Tween TM 80. A commercial preparation of goat anti-rabbit immunoglobulin, coupled to horseradish peroxidase, was diluted 1:4000 in PBS containing 0.025% Tween TM 80 and 0.2% gelatin, and 50 μl was added to each well. After incubation for 1 to 1.5 hours, the solution was removed and the wells were washed four times with PBS containing 0.025% Tween ™ 80. The ABTS Peroxidase Substrate Solutions A and B (Kirkegaard and Perry Laboratories, Gaithersburg, Md.) were freshly mixed in a 1:1 ratio, and 100 μl was added to each plate. The absorbance of each well was determined at 414 nm in a Titertek Multiscan ELISA plate reader 5 to 20 minutes after addition of the substrate. A representative standard curve generated by this assay is shown in FIG. 12.

EXAMPLE 9

Construction of Monoclonal Antibody-Agarose Affinity Columns and Use to Purify rPDGF $B_{v\text{-}sis}$ from Conditioned Media 9(a) Construction of Monoclonal Antibody Affinity Columns: Purified monoclonal antibody immunoglobulins 52 and 162 were coupled to CnBr-activated Sepharose ™ 4B for the development of affinity columns. The coupling was carried out as described in Example 6(d). The ratio of immunoglobulin to Sepharose 4B was 3.5 mg per ml of Sepharose ™ for monoclonal 52, and for 162 it was 3.0 mg/ml.

9(b) Purification of rPDGF B Using Monoclonal Affinity Columns: Affinity purification of rPDGF B from rPDGF B producing cell (for example, CHO-pDSVE/c-sis, CHO-pDSVE/v-sis, or CHO-pDSVE/cv-sis) culture media, may be performed using monoclonal antibody 52 and 162 columns ("Seph 52" and "Seph 162"). The operation of the two monoclonal affinity columns was essentially as described in Example 6 for the rabbit anti-CGP1 immunoglobulin affinity columns. From 0.1 to 3.0 L of CHO rPDGF B culture fluids were adsorbed to the affinity columns (10 ml), washed with buffers F and G at flow rates of 30-40 ml/hour and eluted with 1.0M acetic acid, 0.15M NaCl.

Protein-containing (PDGF) fractions were located by the Bio-Rad protein assay, mitogenic assay for $^3$H-thymidine incorporation, or, in some cases, by dot immunobinding assay. rPDGF B containing fractions were pooled and stored for later analysis as described below.

EXAMPLE 10

Characterization of Purified rPDGF B

10(a) SDS-PAGE analysis of unlabeled and labeled rPDGF B: To assess the purity of rPDGF B chromatographed on Seph 52 or Seph 162 affinity columns, it was analyzed by SDS-PAGE. Unlabeled rPDGF B was detected by silver staining, a technique which permits detection of small quantities of a protein, or by staining with Coomassie Brilliant Blue. Although silver staining is generally a more sensitive method, some proteins are better detected with the Coomassie stain. Typical results revealed the presence only of rPDGF B polypeptides. The sizes of these peptides were the same as those detected when in vivo labeled proteins were immunoprecipitated by anti-PDGF serum from CHO-pDSVE/c-sis medium (Example 4). No other proteins were observed in such highly purified preparations. Since 2 μg protein was loaded on this gel, and the sensitivity under these conditions is 20-50 ng, the purity of the rPDGF B is estimated to be greater than 95%. An immunoblot analysis (see Example 6c) of this rPDGF B preparation, using a rabbit polyclonal antiserum to the CGP1 chicken growth hormone/PDGF fusion protein (Example 5) showed that all of the protein species observed by silver staining were PDGF-related.

Affinity column-purified rPDGF B was iodinated by the method of Bolton and Hunter, ibid. The labeled rPDGF B ($2 \times 10^5$ cpm) was electrophoresed through a SDS-polyacrylamide gel, dried, and exposed to X-ray film for 16 hours. The only bands detected in the autoradiogram corresponded to rPDGF B polypeptides. Since even 50 cpm in a band would have been detectable under these conditions, this analysis shows that the purity of this particular batch of rPDGF B, purified by these methods, was greater than 99%.

10(b) Specific mitogenic activity compared with PDGF from platelets: rPDGF B fractions recovered from the rabbit immunoglobulin affinity column, and pooled fraction samples were tested for biological activity in a mitogenic assay as described in Example 4a. All rPDGF B-containing affinity column fractions were active in the mitogenic assay, and the concentrations calculated from the bioassay standard curve correlated well with the concentrations determined by BioRad protein assay and by dot immunobinding analysis. The specific activity of rPDGF B was similar to several batches of PDGF purified from human platelets.

10(c) N-terminal amino acid sequence analysis: rPDGF B purified as described in Example 10 was subjected to N-terminal sequence analysis and the first 14 amino acids of rPDGF $B_{c\text{-}sis}$ were identified as Ser-Leu-Gly-Ser-Leu-Thr-Ile-Ala-Glu-Pro-Ala-Met-Ile-Ala. These are the same 14 amino acids which occur at the N-terminus of the B chain of PDGF purified from human platelets (Johnsson et al, supra). Small percentages of the amino termini began at amino acid number 33 (Thr-Asn-Ala-Asn-Phe) and at amino acid number 80 (Lys-Lys-Pro-Ile-Phe), also similar to the results found with PDGF purified from platelets (Johnsson et al., supra). The amino terminal sequencing results of rPDGF $B_{v\text{-}sis}$ was similar, with the exception that amino acids number 6 and 7 were Ser-Val instead of Thr-Ile, in agreement with previously published results (Devare et al, ibid.). These results indicate that rPDGF B is processed at its amino terminus in CHO cells in the same manner as it is in human platelets.

The small amounts of amino termini beginning at amino acids number 33 and 80 are likely to be the result of the action of specific proteolytic enzymes found inside CHO cells and platelets. For some purposes it may be desirable to obtain a rPDGF B product which does not contain these internal cleavages. This result may be achieved by altering the amino acid sequence at the cleavage sites in a way that prevents recognition by the specific proteolytic enzymes involved. Thus the particular amino acid residues number 32, 33, 79 and/or 80, as well as immediately adjacent residues, may be changed to alternate amino acids by changing the DNA sequence coding for these residues.

10(d) Analysis of carbohydrate content: Glycosylation of proteins may be either of two types. The most common type is N-linked, in which sugar resides are linked to asparagine at sites having the sequence asn-X-thr/ser. In the other type, O-linked glycosylation, sugar resides are linked to serines or threonines; no other consensus sequence for this type of glycosylation has been identified.

PDGF purified from human platelets contains approximately 7% carbohydrate by weight (Deuel et al., *J. Biol. Chem.* 256:8896 (1981)). The distribution of sugar residues between A and B chains is unknown. However, it can be deduced that the B chain does not contain N-linked carbohydrate, since the sequence asn-X-thr/ser does not occur within it. It remains to be determined whether O-linked glycosylation occurs in the B chain of platelet PDGF.

To determine if rPDGF $B_{v\text{-}sis}$ produced by CHO cells contains carbohydrate, two types of analyses were performed. The first analysis monitored changes in the electrophoretic mobility of the protein during SDS-PAGE, following incubation with the glycosidases neuraminidase, endoglycosidase F or O-glycanase. Results of these experiments indicated that only a very minor component of the protein was altered by treatment with these enzymes.

The second form of carbohydrate analysis involved release of sugar residues by acid methanolysis, and quantitation by gas chromatographic analysis, according to the procedure of Zanetta et al., *J. Chromatogr.* 69:291 (1972). The results of this analysis were: fucose, 0.025% wt/wt; galactose, 0.125%; mannose, 0.075%; N-acetylglucosamine, 0.038%; sialic acid, 0.525%.

From these data it may be concluded that rPDGF $B_{v\text{-}sis}$ produced by CHO cells contains less than 1% by weight of carbohydrate.

10(e) Chemotactic properties: PDGF purified from human platelets has been shown to be chemotactic for fibroblasts, smooth muscle cells, granulocytes and monocytes (Deuel et al., *J. Clin. Invest.* 69: 1046 (1982); Seppa et al., *J Cell Bio.* 92: 584 (1982); Grotendorst et al., *Proc. Natl. Acad. Sci. U.S.A.* 78: 3669 (1981). To determine if rPDGF B shares these properties, it was tested in chemotaxis assays as described by Deuel et al., supra. The rPDGF B was found to be chemotactic for all of the above cell types, to a degree equal to PDGF purified from human platelets.

10(f) In vivo activity of rPDGF B: Wound chambers are constructed from 3.0×3.5 cm pieces of stainless steel wire cloth (40 mesh; 0.010 mesh wire). The wire cloth is rolled around a rod to produce a cylinder 3.5 cm in length and 0.95 cm in diameter. One end of the cylinder is compressed to form a blunt end while a silicone rubber septum is attached to the open end. The completed wound chamber is heat sterilized (120° C. for 30 min.) prior to implantation.

Wound chambers are implanted subcutaneously on the dorsum of male Sprague-Dawley rats (350–400 gm) into pockets made by a 2 cm scalpel incision and blunt dissection to the level on the panniculus carnosus. Following implantation of the chambers, the wounds are closed with stainless steel clips. In this manner, each animal receives two chambers at shoulder level and two additional chambers at the level of the hind legs.

Beginning three days after chamber implantation, 0.1 ml control vehicle or 0.1 ml test article is injected into the chamber by penetration of the silicone rubber plug with a hypodermic needle. The pattern of injection is systematically varied among animals to prevent anatomical location of chambers from influencing the results. At 24 hours after the ninth daily injection, the chambers are removed and the contents scraped out onto a tared weighing boat for determination of net weight. In addition, total protein is determined by the BioRad protein assay, total DNA by the method of Vytasek, *Anal. Biochem.* 120: 243 (1982), and total hydroxyproline by the method of Berg, *Methods Enzymol.* 82: 372 (1982).

Table II shows the effect of daily administration of 5.0 μg rPDGF $B_{c\text{-}sis}$ on the accumulation of granulation tissue within the wound chambers. The data show that the total net weight of accumulated tissue was almost three-fold higher than that obtained from chambers injected with control vehicles. Similar increases were noted in the total amounts of protein, DNA and hydroxyproline deposited within the chambers.

TABLE II

Effect of rPDGF $B_{c\text{-}sis}$ on the Accumulation of Granulation Tissue in Wound Chambers

| Treatment | Wet Weight* (mg) | Protein* (mg) | DNA* (mg) | Hydroxy-Proline* (mg) |
|---|---|---|---|---|
| Vehicle | 92 ± 23 | 4.2 ± 0.8 | 125 ± 31 | 254 ± 87 |
| rPDGF B (5.0 μg) | 244 ± 30 | 8.7 ± 0.8 | 444 ± 56 | 697 ± 250 |

*Mean ± S.E.M.

EXAMPLE 11

Demonstration of the Utility of rPDGF B in the Healing of Wounds

Young, 300–350 g adult male Sprague-Dawley rats (Sasco, Inc., Omaha, Nebr.) had 6 cm incisions placed through the skin 1.5 cm on either side of the midline under anasthesia with pentobarbitol (16 mg). A bovine collagen suspension (Xiderm II ™, Collagen Corporation, Palo Alto, Calif.) at 10 mg/ml, either with or without rPDGF B, was applied to the edges of the open wound (0.1 ml/wound). The wounds were coated with three surgical clips. At the time of harvest the entire dorsal skin of the rat was excised. Using a template with parallel surgical blades, two 8 mm strips were harvested between clips for each incision.

The maximum load tolerated by wounded skin was measured with the Tensometer 10. Measurements were performed on strips stretched at 10 mm per minute, with the maximum load recorded on a graph. Breaking strength measurements were not performed on wounds showing evidence of infection, excessive hemorrhage or poor-coaptation (less than 5% of all wounds).

The results of this study, summarized in Table III, indicate that rPDGF B significantly accelerates the gain in tensile strength of healing skin wounds when applied in the described manner at doses >5 μg per wound.

TABLE III

Acceleration of Healing in 5 Day Linear Incision Wounds by rPDGF B

| Growth Factor | Dose (μg/wound) | n | Breaking Strength (grams) | Percent of Control Value | P< |
|---|---|---|---|---|---|
| rPDGF $B_{v\text{-}sis}$ | 20 | 8 | 228 ± 81<br>119 ± 61 | 192 | .005 |
| rPDGF $B_{c\text{-}sis}$ | 10 | 13 | 249 ± 90<br>129 ± 33 | 193 | .025 |
|  | 5 | 10 | 221 ± 72<br>154 ± 40 | 143 | .025 |
|  | 2 | 12 | 215 ± 98<br>161 ± 81 | 133 | .10 |
|  | 1 | 15 | 166 ± 50<br>153 ± 61 | 108 | NS |

Although the present invention has been described herein in terms of particular embodiments, it is understood that variations and improvements will occur to those skilled in the art upon consideration of the disclosure contained herein.

For example, monoclonal antibodies which recognize epitopes present on the A and/or B chains of PDGF (whether v-sis, c-sis or other variants and analogs thereof) may be useful for purification of PDGF. In addition, because PDGF is the major mitogen for connective tissue cells, the highly purified PDGF of the present invention will be useful for stimulating wound healing. PDGF is released from platelets only at the site of wounds and it is both mitotic and chemotactic for connective tissue cells. One study showed greater collagen synthesis in PDGF-treated wounds of rats than when one of several other hormones were applied.

Therefore, it is intended that the present invention include all such variations and improvements which come within the scope of the invention as claimed.

What is claimed is:

1. A method for purifying a polypeptide having a sufficient part of the structural conformation of rPDGF B to provide at least one epitope found in rPDGF $B_{c\text{-}sis}$ or PDGF $B_{v\text{-}sis}$ comprising the steps of:
   (a) contacting a substrate-bound monoclonal antibody specific for an epitope found in the B chain of PDGF with a solution containing said polypeptide and
   (b) eluting said polypeptide from said substrate-bound monoclonal antibody.

2. The method as recited in claim 1 wherein said contacting step comprises the step of passing said solution containing said polypeptide over a column to which is bound said monoclonal antibody.

3. The method as recited in claim 1 wherein said polypeptide is purified to greater than 95% purity as determined by SDS-PAGE.

4. The method as recited in claim 3 wherein said monoclonal antibody is a monoclonal antibody expressed by a hybridoma deposited as ATCC No. HB 9356.

5. The method as recited in claim 3 wherein said monoclonal antibody is a monoclonal antibody expressed by a hybridoma deposited as ATCC No. HB 9357.

6. The method as recited in claim 3 wherein said monoclonal antibody is a monoclonal antibody expressed by a hybridoma deposited as ATCC No. HB 9369.

7. The method as recited in claim 3 wherein said monoclonal antibody is a monoclonal antibody expressed by a hybridoma deposited as ATCC No. HB 9371.

8. A method for purifying a polypeptide having a sufficient part of the structural conformation of rPDGF B to provide at least one epitope found in rPDGF $B_{c\text{-}sis}$ or PDGF $B_{v\text{-}sis}$ comprising the steps of:
   (a) contacting a substrate-bound monoclonal antibody specific for an epitope found in the B chain of PDGF but not the A chain of PDGF with a solution containing said polypeptide and
   (b) eluting said polypeptide from said substrate-bound monoclonal antibody.

9. The method as recited in claim 8 wherein said contacting step comprises the step of passing said solution containing said polypeptide over a column to which is bound said monoclonal antibody.

10. The method as recited in claim 8 wherein said polypeptide is purified to greater than 95% purity as determined by SDS-PAGE.

11. The method as recited in claim 8 wherein said monoclonal antibody is a monoclonal antibody expressed by a hybridoma deposited as ATCC No. HB 9354.

12. The method as recited in claim 8 wherein said monoclonal antibody is a monoclonal antibody expressed by a hybridoma deposited as ATCC No. HB 9355.

13. The method as recited in claim 8 wherein said monoclonal antibody is a monoclonal antibody expressed by a hybridoma deposited as ATCC No. HB 9361.

14. The method as recited in claim 8 wherein said monoclonal antibody is a monoclonal antibody expressed by a hybridoma deposited as ATCC No. HB 9366.

15. The method as recited in claim 8 wherein said monoclonal antibody is a monoclonal antibody expressed by a hybridoma deposited as ATCC No. HB 9367.

16. The method as recited in claim 8 wherein said monoclonal antibody is a monoclonal antibody expressed by a hybridoma deposited as ATCC No. HB 9368.

17. The method as recited in claim 8 wherein said monoclonal antibody is a monoclonal antibody expressed by a hybridoma deposited as ATCC No. HB 9370.

18. The method as recited in claim 8 wherein said monoclonal antibody is a monoclonal antibody expressed by a hybridoma deposited as ATCC No. HB 9372.

* * * * *